United States Patent
Maliverney et al.

(10) Patent No.: US 9,447,258 B2
(45) Date of Patent: Sep. 20, 2016

(54) ORGANOPOLYSILOXANE COMPOSITION SUITABLE FOR VULCANISATION INTO AN ELASTOMER AT ROOM TEMPERATURE AND NEW ORGANOPOLYSILOXANE POLYCONDENSATION CATALYSTS

(71) Applicant: BLUESTAR SILICONES FRANCE SAS, Lyons (FR)

(72) Inventors: Christian Maliverney, Saint Julien sur Bibost (FR); Delphine Blanc, Lyons (FR); Michel Feder, Villeurbanne (FR); Delphine Platel, Saint Maurice de Gourdans (FR)

(73) Assignee: BLUESTAR SILICONES FRANCE SAS, Lyons (FR)

(*) Notice: Subject to any disclaimer, the term of this patent is extended or adjusted under 35 U.S.C. 154(b) by 0 days.

(21) Appl. No.: 14/652,948

(22) PCT Filed: Dec. 17, 2013

(86) PCT No.: PCT/FR2013/000345
§ 371 (c)(1),
(2) Date: Jun. 17, 2015

(87) PCT Pub. No.: WO2014/096566
PCT Pub. Date: Jun. 26, 2014

(65) Prior Publication Data
US 2015/0337115 A1    Nov. 26, 2015

(30) Foreign Application Priority Data
Dec. 20, 2012 (FR) ..................... 12 03517

(51) Int. Cl.
| | | |
|---|---|---|
| *C08G 77/04* | (2006.01) |
| *C08K 5/5415* | (2006.01) |
| *C08K 3/36* | (2006.01) |
| *C07F 3/06* | (2006.01) |
| *C07F 7/18* | (2006.01) |
| *B05D 3/04* | (2006.01) |
| *C09D 183/04* | (2006.01) |
| *C08G 77/08* | (2006.01) |
| *C08G 77/14* | (2006.01) |
| *C08L 83/04* | (2006.01) |
| *B01J 31/04* | (2006.01) |
| *B01J 31/12* | (2006.01) |

(52) U.S. Cl.
CPC .............. *C08K 5/5415* (2013.01); *B01J 31/04* (2013.01); *B01J 31/122* (2013.01); *B05D 3/0406* (2013.01); *C07F 3/06* (2013.01); *C07F 7/1836* (2013.01); *C08G 77/08* (2013.01); *C08G 77/14* (2013.01); *C08K 3/36* (2013.01); *C08L 83/04* (2013.01); *C09D 183/04* (2013.01); *B01J 2231/14* (2013.01); *Y02P 20/52* (2015.11)

(58) Field of Classification Search
None
See application file for complete search history.

(56) References Cited

U.S. PATENT DOCUMENTS

| 3,127,363 | A | | 3/1964 | Nitzsche | |
|---|---|---|---|---|---|
| 4,410,677 | A | * | 10/1983 | Lampe | .................. C08K 5/098 524/265 |
| 6,245,952 | B1 | | 6/2001 | Mimoun | |
| 6,573,395 | B2 | * | 6/2003 | Mimoun | .............. B01J 31/1805 502/162 |
| 2007/0203297 | A1 | * | 8/2007 | Wakabayashi | ...... C08F 293/005 525/187 |
| 2008/0207938 | A1 | | 8/2008 | Prasse | |
| 2009/0092840 | A1 | * | 4/2009 | Schlumpf | .............. C08G 18/10 428/423.1 |
| 2011/0046304 | A1 | | 2/2011 | Maliverney | |
| 2014/0343202 | A1 | * | 11/2014 | Dinkar | ................. B01J 31/2234 524/141 |
| 2014/0378612 | A1 | * | 12/2014 | Dinkar | .................... C08L 83/04 524/860 |

FOREIGN PATENT DOCUMENTS

| EP | 147323 | A2 | 7/1985 |
|---|---|---|---|
| EP | 235049 | A1 | 9/1987 |
| FR | 2557582 | A1 | 7/1985 |
| FR | 2786497 | A1 | 6/2000 |
| GB | 859724 | A | 1/1961 |

OTHER PUBLICATIONS

International Search Report from corresponding PCT/FR2013/000345, mailed Apr. 29, 2014.
Noll, "Chemistry and Technology of Silicones", Chapter 8, Leverkusen, Germany, 1968, pp. 386-436.

* cited by examiner

*Primary Examiner* — Robert S Loewe
(74) *Attorney, Agent, or Firm* — McBee Moore Woodward & Vanik IP, LLC

(57) ABSTRACT

The present invention relates to an organopolysiloxane composition which is suitable for vulcanization into an elastomer as from room temperature, and which crosslinks via polycondensation, as well as to new organopolysiloxane polycondensation catalysts.

22 Claims, No Drawings

ORGANOPOLYSILOXANE COMPOSITION SUITABLE FOR VULCANISATION INTO AN ELASTOMER AT ROOM TEMPERATURE AND NEW ORGANOPOLYSILOXANE POLYCONDENSATION CATALYSTS

CROSS REFERENCE TO RELATED APPLICATIONS

This application is a §371 National Stage Application of PCT/FR 2013/000345, filed 17 Dec. 2013, which claims priority to FR 12 03517, filed 20 Dec. 2012.

BACKGROUND

1. Field of the Invention

The present invention relates to a composition comprising at least one organosilicon compound A comprising at least two hydrolyzable and condensable groups, which may be identical or different, or at least two silanol functions ≡SiOH, which are crosslinkable, curable or vulcanizable at room temperature into elastomer by polycondensation and which do not contain any alkyltin-based catalysts that have toxicity problems.

2. Description of Related Art

The invention also relates to novel polycondensation catalysts in the chemistry of silicon compounds and in particular in the chemistry of silicones and to the uses thereof as catalysts for the polycondensation reaction of silicon compounds comprising at least two identical or different hydrolyzable and condensable groups, or at least two silanol functions ≡SiOH.

Formulations of silicone compositions that crosslink via polycondensation generally involve a silicone oil, generally a polydimethylsiloxane, with hydroxyl end groups, optionally prefunctionalized with a silane so as to have hydrolyzable and condensable ends, a crosslinking agent, a polycondensation catalyst, conventionally a tin salt or an alkyl titanate, usually with a reinforcing filler and other optional additives such as bulking fillers, adhesion promoters, colorants, biocidal agents, etc.

These silicone compositions which "cure" by polymerization and/or crosslinking at room temperature are well known to those skilled in the art and are classified into two distinct groups:
one-pack compositions (RTV-1), which are in the form of only one part (or component) whose packaging is airtight, and
two-pack compositions (RTV-2), which are in the form of two distinct parts (hence the name "two-pack") and whose packaging containing the catalyst is airtight.

The purpose of the airtight packagings is to avoid the silicone compositions containing the catalyst from coming into contact with atmospheric moisture during storage before use.

During curing (by polymerization and/or crosslinking) of these silicone compositions, the water is provided by the atmospheric moisture in the case of the RTV-1 products. In the case of the RTV-2 products, dimethyltin dicarboxylates are commonly used as catalysts, but they require the addition of an amount of water to one of the parts in order to activate the catalyst and to allow the polycondensation reaction when the contents of the two parts are mixed in ambient air so as to form the elastomer network, which is reflected by curing of the composition.

For example, the one-pack silicone compositions (RTV-1) used as mastics or adhesives crosslink without heating according to a mechanism involving a certain number of reactions that may be successive or simultaneous:

a) functionalization which results from the placing of a silicone oil bearing silanol functions in contact with a crosslinking agent, occasionally known as a "scavenger", such as a silane compound of $SiX_4$ type (for example a silicate) or a compound bearing the following function —$SiX_3$ with X usually being an alkoxy, acyloxy, amino, amido, enoxy, aminoxy, ketiminoxy or oxime function, which are well known for being reactive with silanol functions. The resulting product is usually known as a "functionalized oil". This reaction may be desired directly during the preparation of the composition or optionally as a pre-step before the addition of the other components of the composition. In this pre-step, it is common practice to use a functionalization catalyst, for instance lithium hydroxide or potassium hydroxide so as to give the one-pack composition good stability on storage. To do this, a person skilled in the art may choose specific functionalization catalysts and will adjust the amount of the reagents so as to have a molar excess of crosslinking agent relative to the silanol functions to be functionalized, and b) crosslinking via a hydrolysis of the functionalized oil generally performed by means of water vapor which diffuses into the material from the surface exposed to the atmosphere, and a condensation between the silanol groups formed and other residual reactive functions.

Generally, the polycondensation reaction kinetics are slow. These reactions are thus catalyzed with a suitable catalyst. As catalysts that are used, use is most often made of catalysts based on tin, titanium, an amine or compositions of these catalysts. Catalysts based on tin (cf. in particular FR-A-2 557 582) and on titanium (cf. in particular FR-A-2 786 497) are catalysts that are effective.

As regards the RTV-2 two-pack compositions, they are sold and stored in the form of two components (or parts), a first component (or part) comprising the polymers that are capable of polycondensing and the second component is airtight and contains the catalyst and usually the crosslinking agent. The two components (or parts) are mixed during use and the mixture crosslinks in the form of a relatively hard elastomer when the composition comprises reinforcing fillers. These two-pack compositions are well known and are described, in particular, in the book by Walter Noll "Chemistry and Technology of Silicones" 1968, 2nd Edition, on pages 395 to 398. These compositions essentially comprise 4 different ingredients:
a reactive polymer such as an α,ω-bis(hydroxydimethylsilyl)polydimethylsiloxane,
a crosslinking agent,
a condensation catalyst, and
optionally water, which is usually present when a dialkyltin dicarboxylate is used as catalyst (activation of this catalyst by the presence of water).

Usually, the condensation catalyst is based on an organic tin compound. Indeed, many tin-based catalysts have already been proposed as a catalyst for crosslinking these RTV-2 products. The most widely used compounds are alkyltin carboxylates such as tributyltin monooleate or dialkyltin dicarboxylates such as dibutyltin dilaurate, dibutyltin diacetate or dimethyltin dilaurate (see the book by Noll "Chemistry and Technology of silicones" page 337, Academic Press, 1968—2nd Edition or patents EP 147 323 or EP 235 049).

However, the alkyltin-based catalysts, although very effective, usually colorless, liquid and soluble in silicone oils, have the drawback of being toxic (CMR2 toxic for reproduction).

Titanium-based catalysts, which are also extensively used in RTV-1 products, have, however, a major drawback: they have slower kinetics than tin-based catalysts. Furthermore, these catalysts cannot be used in RTV-2 compositions due to gelling problems.

Other catalysts are sometimes mentioned, such as catalysts based on zinc, zirconium or aluminum, but they have only experienced minor industrial development due to their mediocre effectiveness.

For sustainable development, it therefore appears necessary to develop nontoxic catalysts for the polycondensation reaction of organopolysiloxanes.

Another important aspect for an organopolysiloxane polycondensation reaction catalyst is the pot life, that is to say the time during which the composition can be used after mixing without curing. This time must be long enough to allow it to be used, but short enough to obtain a molded article that can be handled at the latest a few minutes or a few hours after it has been manufactured. The catalyst must thus make it possible to obtain a good compromise between the pot life of the catalyzed mixture and the time at the end of which the molded article can be handled (these times depend on the targeted application such as, for example, the molding or manufacture of seals). In addition, the catalyst must confer, on the catalyzed mixture, a spreading time which does not vary as a function of the storage time.

SUMMARY

The essential objective of the present invention is therefore to find novel catalysts that enable, in atmospheric moisture, both surface crosslinking and core crosslinking that is as complete as possible when they are used in RTV-1 one pack compositions.

Another essential objective of the present invention is to propose a catalyst that can be used both in the crosslinking of crosslinkable compositions into elastomer and which are in the form of a one-pack (RTV-1) or two-pack (RTV-2) composition.

Another essential objective of the present invention is to propose a catalytic system that continues simultaneously to meet the constraints of storage, of processing and of crosslinking of the two types of one-pack and two-pack elastomer compositions.

These objectives, among others, are achieved by the present invention, which relates firstly to a composition comprising:
  at least one organosilicon compound A comprising at least two identical or different hydrolyzable and condensable groups, or at least two silanol functions ≡SiOH,
  at least one crosslinking agent B,
  optionally at least one filler C, and
  a catalytically effective amount of at least one polycondensation catalyst M which is a zinc complex comprising in its structure two types of ligand: carboxylate and amine.

DETAILED DESCRIPTION OF A PREFERRED EMBODIMENT

Preferentially, the polycondensation catalyst M is a zinc complex comprising in its structure at least two carboxylate ligands and at least one amine ligand, and even more preferentially, the polycondensation catalyst M is a zinc complex comprising in its structure:
  at least two identical or different carboxylate ligands, and
  one or two amine ligands.

It is understood that the term "complex" includes in its definition any monomeric, oligomeric or similar form of said zinc complex according to the invention.

The inventors have, to their credit, found, entirely surprisingly and unexpectedly, that use should be made of zinc metal complexes comprising two specific types of ligands, namely carboxylate and amine ligands, to achieve crosslinking rates that are much more effective than those of zinc dicarboxylate complexes, which, nevertheless, have structural similarities.

The inventors have also, to their credit, overcome the technical prejudice that hitherto maintained that certain complexes of metals, for instance zinc, have only mediocre activity in the polycondensation reaction of organopolysiloxanes.

The definition of the ligands is taken from the book "Chimie Organométallique" [Organometallic Chemistry] by Didier Astruc, published in 2000 by EDP Sciences: see, in particular, Chapter 1, "Les complexes monométalliques" [Single-metal complexes], pages 31 et seq.

The catalyst according to the invention may be in the solid or liquid state. It may be incorporated alone or in a suitable solvent. When it is in solvent, a silicone oil or any other compatible solvent such as petroleum fractions may be added, and the solvent is then evaporated so as to transfer the catalyst into a silicone medium. The mixture obtained may then serve as a "catalyzing base".

According to a preferred embodiment, the polycondensation catalyst(s) M may be obtained:
a) by reacting per 1 mol of at least one zinc dicarboxylate of formula [Zn(carboxylate)$_2$] or of a mixture of two different zinc dicarboxylates $X^1$ mol of amine or a mixture of amines optionally in the presence of a solvent, so as to obtain a reaction product comprising:
  x mol of a zinc complex A which is a [(Zn(carboxylate)$_2$(amine)] complex,
  y mol of a zinc complex B which is a [(Zn(carboxylate)$_2$(amine)$_2$] complex,
  with x≥0, y≥0,
  optionally $X^3$ mol of unreacted zinc dicarboxylate, and
  optionally $X^4$ mol of residual unreacted amine, and
b) after optionally removing the solvent and the residual amine, the polycondensation catalyst(s) M are recovered in the form of at least one zinc complex A, at least one zinc complex B or a mixture of zinc complex A and of zinc complex B, with optionally a residual amount of $X^3$ mol of the complex [Zn(carboxylate)$_2$], and
  the symbols $X^1$, $X^3$ and $X^4$ are numbers and the sum $x+y+X^3=1$.

The removal of the solvent or of the residual amine will be performed via any known technique (distillation, filtration, etc.). It is known that structures [Zn(carboxylate)$_2$(amine)] or [Zn(carboxylate)$_2$(amine)$_2$] may also form dimers, trimers or tetramers. Consequently, the definition of the catalyst according to the invention also includes the dimeric, trimeric or tetrameric forms of said catalyst according to the invention.

Depending on the type of polycondensation catalyst M desired (monoamino or diamino zinc dicarboxylate complex, or a mixture of these species), the number of moles of amine $X^1$ will be adjusted in consequence:

$X^1 \geq 2$ molar equivalents relative to the zinc, so as to obtain predominantly a zinc diamine dicarboxylate complex B, $1 \geq X^1 < 2$ molar equivalents relative to the zinc, so as to obtain predominantly a mixture of zinc diamine dicarboxylate complex B and zinc monoamine dicarboxylate A, $X^1 < 1$ molar equivalent relative to the zinc, so as to obtain predominantly a mixture of zinc monoamine dicarboxylate complex A and of unreacted complex [Zn(carboxylate)$_2$].

The complexes of zinc dicarboxylate type are mostly commercially available or may be readily prepared, for example by adding zinc chloride in methanolic solution to a solution of sodium carboxylate in a solvent such as a toluene-methanol mixture. After distilling off the methanol, filtering off the sodium chloride formed and evaporating off the toluene, the corresponding zinc dicarboxylate is obtained.

Another known method consists in pouring a sodium carboxylate into a solution of zinc nitrate while keeping the pH of the solution in the region of 5 and optionally at a temperature in the region of 40° C. The precipitate obtained is then filtered off, optionally washed with distilled water and then dried so as to obtain the corresponding zinc dicarboxylate.

To prepare mixed zinc dicarboxylate complexes, i.e. with two different types of carboxylate ligands, two types of sodium carboxylates may be simultaneously added in equimolar proportion or otherwise to the zinc nitrate in aqueous solution. The reaction product is a mixed zinc dicarboxylate optionally in hydrated form.

According to a preferred embodiment, the invention relates to a composition comprising:

at least one organosilicon compound A comprising at least two identical or different hydrolyzable and condensable groups, or at least two silanol functions ≡SiOH, at least one crosslinking agent B, optionally at least one filler C, and a catalytically effective amount of at least one polycondensation catalyst M which is a complex of formula (1) below:

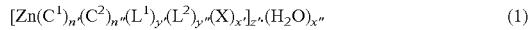  (1)

in which:
the symbols $C^1$ and $C^2$ are identical or different ligands chosen from the group of carboxylates,
the symbols n' and n" represent the number of carboxylate ligands and are integers equal to 0, 1 or 2 with the condition that the sum n'+n"=2,
the symbols $L^1$ and $L^2$ are identical or different ligands chosen from the group of amines,
the symbols y' and y" represent the number of amine ligands and are integers equal to 0, 1 or 2 with the condition that the sum y'+y"=1 or 2,
the symbol X is a ligand other than $C^1$, $C^2$, $L^1$ and $L^2$ and preferably a neutral ligand other than an amine and even more preferentially X is an $H_2O$ molecule,
the symbol x'≥0, and preferably x'=0, 1, 2, 3 or 4,
the symbol x"≥0, and preferably x"=0, 1, 2, 3 or 4, and
the symbol z' is an integer greater than or equal to 1 and preferably z'=1 or 2.

The ligand X is preferably a neutral ligand other than an amine, and the structure of which is of little importance. A person skilled in the art will use any type of precursor during the preparation of the catalyst M according to the invention such that this neutral ligand does not interfere with the reactivity of the catalyst. An example of a neutral ligand is, for example, a water molecule.

According to a preferred embodiment, the polycondensation catalyst M is a complex of formula (2) below:

  (2)

in which:
the symbols $C^1$ and $C^2$ are identical or different ligands chosen from the group of carboxylates,
the symbols n' and n" represent the number of carboxylate ligands and are integers equal to 0, 1 or 2 with the condition that the sum n'+n"=2,
the symbols $L^1$ and $L^2$ are identical or different ligands chosen from the group of amines,
the symbols y' and y" represent the number of amine ligands and are integers equal to 0, 1 or 2 with the condition that the sum y'+y"=1 or 2, and
the symbol z' is an integer greater than or equal to 1 and preferably z'=1 or 2 and even more preferentially z'=1.

According to another preferred embodiment, the polycondensation catalyst M is a complex of formula (3) below:

  (3)

in which:
the symbol $C^1$ is a ligand chosen from the group of carboxylates,
the symbol $L^1$ is a ligand chosen from the group of amines,
the symbol y' is a number equal to 1 or 2, and
the symbol z' is an integer greater than or equal to 1 and preferably the symbol z'=1, 2, 3 or 4 and even more preferentially z'=1 or 2.

Examples of amines that are useful as ligands $L^1$ or $L^2$ are, for example, the following amidines: N'-cyclohexyl-N,N-dimethylformamidine, N'-methyl-N,N-di-n-butylacetamidine, N'-octadecyl-N,N-dimethylformamidine, N'-cyclohexyl-N,N-dimethylvaleramidine, 1-methyl-2-cyclohexyliminopyrrolidine, 3-butyl-3,4,5,6-tetrahydropyrimidine, N-(hexyliminomethyl)morpholine, N-([α]-(decyliminoethyl)ethyl)pyrrolidine, N'-decyl-N,N-dimethylformamidine, N'-dodecyl-N,N-dimethylformamidine, N'-cyclohexyl-N,N-acetamidine.

Other amines that are useful as ligands are, for example, heterocyclic derivatives of imidazoline, imidazole, tetrahydropyrimidine, dihydropyrimidine, pyridine, pyrrolidine, piperidine or pyrimidine type. Use may also be made of acyclic amidines or guanidines.

Examples of imidazole ligands are the following compounds: N-(2-hydroxyethyl)imidazole, N-(3-aminopropyl)imidazole, 4-(hydroxymethyl)imidazole, 1-(tert-butoxycarbonyl)imidazole, 4-carboxyimidazole, 1-butylimidazole, 4-formylimidazole, 1-(ethoxycarbonyl)imidazole, 2-methylimidazole, 1-trimethylsilylimidazole, 1-(p-toluenesulfonyl)imidazole, 1,1'-carbonylbisimidazole and 1-(2-cyanoethyl)-2-ethyl-4-methylimidazole.

Examples of imidazole ligands are the following compounds: 1H-imidazole-1-ethanol, 2-(8Z)-8-heptadecenyl-4,5-dihydro, 1H-imidazole-1-ethanol, 1H-imidazole-1-ethanol, 1H-imidazole, 4,5-dihydro, -2-(9Z)-9-octadecenyl, oleyl hydroxyethylimidazoline, 1H-imidazole-1-ethanol, 4,5-dihydro-2-undecyl-, 1H-imidazole-1-ethanol, 2-heptadecyl-4,5-dihydro and 1H-imidazole-1-ethanol, 2-nonyl-4,5-dihydro.

Preferably, the ligand of amine type $L^1$ or $L^2$ is chosen from the group consisting of primary monoamines of alkylamine type containing in total from 1 to 40 carbon atoms for the alkyl radical, secondary monoamines of dialkylamine type containing in total from 2 to 40 carbon atoms for the alkyl radicals, tertiary monoamines of trialkylamine type containing in total from 3 to 60 carbon atoms for the alkyl radicals, alkyl diamines containing in total from 1 to 40 carbon atoms for the alkyl radicals and amino silanes, and even more preferentially the ligands $L^1$ and $L^2$ are chosen from the group consisting of secondary monoamines of dialkylamine type containing in total from 2 to 20 carbon atoms and primary monoamines of alkylamine type containing in total from 1 to 40 carbon atoms for the alkyl radical.

Ligands $L^1$ or $L^2$ that are useful according to the invention are the amines chosen from the group consisting of the following amines: N,N-dimethylethylenediamine, N,N'-dimethylethylenediamine, N,N,N'-trimethylethylenediamine, N,N'-diisopropylethylenediamine, n-butylamine, n-propylamine, n-heptylamine, n-octylamine, n-nonylamine, tert-butylamine, isopropylamine, 2-ethylhexylamine, decylamine, dodecylamine, which may be linear or branched, N-methyl-N-butylamine, N,N-dipropylamine, N,N-diisopropylamine, N-ethyl-N-butylamine, N,N-dibutylamine, N,N-dimethyl-N-butylamine, di(n-octyl)amine, N-n-propylethylenediamine, N,N,N',N'-tetramethylethylenediamine, 3-aminopropyltrimethoxysilane and 3-aminopropylmethyldiethoxysilane.

Another list of ligands that are useful according to the invention is the following list of amines:

Primary amines: N-propylamine, N-isopropylamine, N-butylamine, N-benzylamine, N-hexylamine, N-cyclohexylamine, N-n-octylamine, N-(2-ethylhexyl)amine, N-(2-phenylethyl)amine, N-(3-methoxypropyl)amine, N-nonylamine, N-isononylamine, N-decylamine, N-dodecylamine, ethylenediamine and 1,3-diaminopropane.

Secondary amines: N,N-dipropylamine, N,N-diisopropylamine, N,N-dibutylamine, N,N-dihexylamine, N,N-dicyclohexylamine, N,N-bis(2-methoxyethyl)amine, N,N-dioctylamine, N,N-bis(2-ethylhexyl)amine, N,N-diisononylamine, N,N-bis(tridecyl)amine, morpholine, piperidine, pyrrolidine, 2,2,6,6-tetramethylpiperidine, piperazine, N,N'-dimethylethylenediamine, N,N'-diethylethylenediamine and N,N'-diisopropylethylenediamine.

The carboxylate ligands $C^1$ and $C^2$ that are useful according to the invention are, for example:

anions derived from aliphatic carboxylic acids such as the following anions: methoxide or formate $[H—COO]^-$, ethoxide or acetate $[CH_3—COO]^-$, propanoate or propionate $[CH_3CH_2—COO]^-$, butanoate or butyrate $[CH_3—(CH_2)_2—COO]^-$, pentanoate or valerate $[CH_3—(CH_2)_3—COO]^-$, hexanoate or caproate $[CH_3—(CH_2)_4—COO]^-$, heptanoate $[CH_3—(CH_2)_5—COO]^-$, octanoate $[CH_3—(CH_2)_6—COO]^-$, 2-ethylhexanoate $[CH_3—(CH_2)_4—CH(C_2H_5)—COO]^-$, nonanoate $[CH_3—(CH_2)_7—COO]^-$, decanoate $[CH_3—(CH_2)_8—COO]^-$, undecanoate $[CH_3—(CH_2)_9—COO]^-$, dodecanoate or laurate $[CH_3—(CH_2)_{10}—COO]^-$, tridecanoate $[CH_3—(CH_2)_{11}—COO]^-$, tetradecanoate or myristate $[CH_3—(CH_2)_{12}—COO]^-$, pentadecanoate $[CH_3—(CH_2)_{13}—COO]^-$, hexadecanoate or palmitate $[CH_3—(CH_2)_{14}—COO]^-$, heptadecanoate $[CH_3—(CH_2)_{15}—COO]^-$, octadecanoate or stearate $[CH_3—(CH_2)_{16}—COO]^-$, nonadecanoate $[CH_3—(CH_2)_{17}—COO]^-$, eicosanoate $[CH_3—(CH_2)_{18}—COO]^-$, heneicosanoate $[CH_3—(CH_2)_{19}—COO]^-$, docosanoate or behenate $[CH_3—(CH_2)_{20}—COO]^-$, tricosanoate $[CH_3—(CH_2)_{21}—COO]^-$, tetracosanoate or lignocerate $[CH_3—(CH_2)_{22}—COO]^-$, pentacosanoate $[CH_3—(CH_2)_{23}—COO]^-$, hexacosanoate $[CH_3—(CH_2)_{24}—COO]^-$, heptacosanoic acid $[CH_3—(CH_2)_{25}—COO]^-$, octacosanoate $[CH_3—(CH_2)_{26}—COO]^-$, nonacosanoate $[CH_3—(CH_2)_{27}—COO]^-$, triacontanoate $[CH_3—(CH_2)_{28}—COO]^-$, hentriacontanoate $[CH_3—(CH_2)_{29}—COO]^-$, dotriacontanoate $[CH_3—(CH_2)_{30}—COO]^-$, palmitoleate $[CH_3—(CH_2)_5—CH=CH—(CH_2)_7—COO]^-$, oleate $[CH_3(CH_2)_7CH=CH(CH_2)_7COO]^-$, linoleate $[CH_3—(CH_2)_4—(CH=CHCH_2)_2—(CH_2)_6—COO]^-$, linolenate $[CH_3—CH_2—(CH=CHCH_2)_3—(CH_2)_6—COO]^-$, arachidonate $[CH_3—(CH_2)_4—(CH=CHCH_2)_4—(CH_2)_2—COO]^-$, the following $C_{10}$ structural isomers, taken alone or as a mixture (neodecanoate): 7,7-dimethyloctanoate $[(CH_3)_3C—(CH_2)_5—COO]^-$, 2,2-dimethyloctanoate $[CH_3—(CH_2)_5—C(CH_3)_2—COO]^-$, 2,2,3,5-tetramethylhexanoate $[(CH_3)_2CH—CH_2—CH(CH_3)—C(CH_3)_2—COO]^-$, 2,5-dimethyl-2-ethylhexanoate $[(CH_3)_2CH—(CH_2)_2—C(CH_3)(C_2H_5)—COO]^-$, 2,2-diethylhexanoate $[CH_3—(CH_2)_3—C(C_2H_5)_2—COO]^-$, 2,4-dimethyl-2-isopropylpentanoate $[(CH_3)_2CH—CH_2—C(CH_3)(i\text{-propyl})\text{-}COO]^-$, the carboxylates corresponding to Versatic™ 10 acid (sold by the company Momentive) of empirical formula $[C_{10}H_{19}O_2]^-$ and of linear formula $[(R^1)(R^2)C(CH_3)—COO]^-$ with the symbols $R^1$ and $R^2$ which are alkyls, or anions derived from aromatic carboxylic acids such as anions of benzoate, phenylacetate, phenylpropionate, phenylbutyrate or naphthenate type.

The term "aliphatic" means that it is a saturated or unsaturated, linear or branched, acyclic or cyclic carbon-based organic compound, with the exclusion of aromatic compounds.

It is particularly advantageous to choose carboxylate ligands of empirical formula $[C_{10}H_{19}O_2]^-$ and it is even more preferentially advantageous to choose neodecanoate as ligand of carboxylate type.

According to another preferred embodiment, the symbols $C^1$ and $C^2$ are identical or different carboxylate ligands chosen from the group of anions of empirical formula $[C_nH_{2n-1}O_2]^-$, in which formula the symbol n is an integer from 1 to 40, preferably from 1 to 32 and even more preferentially from 2 to 30.

According to a preferred embodiment, the ligand of carboxylate type $C^1$ or $C^2$ is chosen from the group consisting of the carboxylates of empirical formula $[C_{10}H_{19}O_2]^-$.

According to another preferred embodiment, the polycondensation catalyst M is a complex of formula (3') below:

$$[Zn(C^1)_2(L^1)_{y'}]_{z'} \qquad (3')$$

in which:

the symbol $C^1$ is a neodecanoate or naphthenate ligand or a 2-ethylhexanoate ligand, the symbol L is a ligand chosen from the group consisting of the following compounds: N,N-dimethylethylenediamine, N,N'-dimethylethylenediamine, N,N,N'-trimethylethylenediamine, N,N'-diisopropylethylenediamine, n-butylamine, n-propylamine, n-heptylamine, n-octylamine, n-nonylamine, tert-butylamine, isopropylamine, 2-ethylhexylamine, decylamine, dodecylamine, which may be linear or branched, N-methyl-N-butylamine, N,N-dipropylamine, N,N- diisopropylamine, N-ethyl-N-butylamine, N,N-dibutylamine, N,N-dimethyl-N-butylamine, di(n-octyl)amine, N-n-propylethylenediamine, N,N'-dimethylethylenediamine, N,N,N',N'-tetramethylethylenediamine, 3-aminopropyltrimethoxysilane and 3-aminopropylmethyldiethoxysilane, the symbol y' is an integer equal to 1 or 2, and the symbol z'=1, 2, 3 or 4 and preferably z'=1 or 2.

A polycondensation catalyst M that is particularly advantageous according to the invention is a complex chosen from the group consisting of the following complexes:

[Zn(naphthenate)$_2$ (bis(2-ethylhexyl)amine)],
[Zn(naphthenate)$_2$ (bis(2-ethylhexyl)amine)$_2$],
[Zn(naphthenate)$_2$ (diisononylamine)],
[Zn(naphthenate)$_2$ (diisononylamine)$_2$],
[Zn(naphthenate)$_2$ (di(n-octyl)amine)],
[Zn(naphthenate)$_2$ (di(n-octyl)amine)$_2$],
[Zn(naphthenate)$_2$(n-octylamine)],
[Zn(naphthenate)$_2$(n-octylamine)$_2$],
[Zn(naphthenate)$_2$(N,N-dibutylamine)],
[Zn(naphthenate)$_2$(N,N-dibutylamine)$_2$],
[Zn(naphthenate)$_2$(N,N-dimethyl-N-butylamine)$_2$],
[Zn(naphthenate)$_2$(N,N-dimethyl-N-butylamine)$_2$],
[Zn(naphthenate)$_2$(aminoethylaminopropyltrimethoxysilane)],
[Zn(naphthenate)$_2$(aminoethylaminopropyltrimethoxysilane)$_2$],
[Zn(naphthenate)$_2$(aminopropyltriethoxysilane)],
[Zn(naphthenate)$_2$(aminopropyltriethoxysilane)$_2$],
[Zn(neodecanoate)$_2$(di(n-octyl)amine)],
[Zn(neodecanoate)$_2$(di(n-octyl)amine)]$_2$],
[Zn(neodecanoate)$_2$(n-octylamine)],
[Zn(neodecanoate)$_2$(n-octylamine)$_2$],
[Zn(neodecanoate)$_2$(N,N-dibutylamine)],
[Zn(neodecanoate)$_2$(N,N-dibutylamine)$_2$],
[Zn(neodecanoate)$_2$(3-aminopropyltrimethoxysilane)$_2$],
[Zn(neodecanoate)$_2$ (3-aminopropylmethyldiethoxysilane)$_2$],
[Zn(neodecanoate)$_2$ (aminoethylaminopropyltrimethoxysilane)],
[Zn(neodecanoate)$_2$ (aminoethylaminopropyltrimethoxysilane)$_2$],
[Zn(neodecanoate)$_2$ (aminopropyltriethoxysilane)],
[Zn(neodecanoate)$_2$ (aminopropyltriethoxysilane)$_2$],
[Zn(neodecanoate)$_2$ (bis(2-ethylhexyl)amine)],
[Zn(neodecanoate)$_2$ (bis(2-ethylhexyl)amine)$_2$],
[Zn(neodecanoate)$_2$ (diisononylamine)],
[Zn(neodecanoate)$_2$ (diisononylamine)$_2$],
[Zn(2-ethylhexanoate)$_2$(N,N-dibutylamine)]
[Zn(2-ethylhexanoate)$_2$(N,N-dibutylamine)$_2$],
[Zn(2-ethylhexanoate)$_2$(n-octylamine)],
[Zn(2-ethylhexanoate)$_2$(n-octylamine)$_2$],
[Zn(2-ethylhexanoate)$_2$ (bis(2-ethylhexyl)amine)],
[Zn(2-ethylhexanoate)$_2$ (bis(2-ethylhexyl)amine)$_2$],
[Zn(2-ethylhexanoate)$_2$ (diisononylamine)],
[Zn(2-ethylhexanoate)$_2$ (diisononylamine)$_2$] and
mixtures thereof.

Preferably, the amount of polycondensation catalyst M according to the invention is between 0.1% and 10% by weight relative to the total weight of the composition, preferably between 0.5% and 5%, whether it is a one-pack or two-pack preparation.

The organosilicon compounds A according to the invention may be an organosilane, an organosiloxane, an organopolysiloxane comprising at least two hydrolyzable and condensable groups, or at least two silanol functions ≡SiOH, or mixtures of such organosilicon compounds.

Preferably, the organosilicon compound A according to the invention will bear at least two groups chosen from the group consisting of groups such as hydroxyl, alkoxy, alkoxy-alkylene-oxy, amino, amido, acylamino, aminoxy, iminoxy, ketiminoxy, acyloxy and enoxy.

According to one embodiment, the organosilicon compound A is a polyorganosiloxane comprising:

(i) at least two siloxyl units of formula (4) below:

(4)

in which:
the symbols $R^1$, which may be identical or different, represent $C_1$ to $C_{30}$ monovalent hydrocarbon-based radicals,
the symbols Z, which may be identical or different, each represent a hydrolyzable and condensable group or a hydroxyl group and are preferably chosen from the group consisting of groups of the following types: hydroxyl, alkoxy, alkoxy-alkylene-oxy, amino, amido, acylamino, aminoxy, iminoxy, ketiminoxy, acyloxy and enoxy,
a is equal to 0, 1 or 2, b is equal to 1, 2 or 3, the sum a+b is equal to 1, 2 or 3, and optionally (ii) one or more siloxyl units of formula (5) below:

(5)

in which:
the symbols R, which may be identical or different, represent $C_1$ to $C_{30}$ monovalent hydrocarbon-based radicals optionally substituted with one or more halogen atoms or with amino, ether, ester, epoxy, mercapto, cyano or (poly)glycol groups, and
the symbol c is equal to 0, 1, 2 or 3.

Another important aspect for a composition that is crosslinkable via condensation reactions is the working time (pot life), that is to say the time during which the composition may be used after mixing without curing. For example, in a molding application, this time must be long enough to allow it to be used, but short enough to obtain a molded article that can be handled at the latest a few minutes or a few hours after it has been manufactured. The catalyst must thus make it possible to obtain a good compromise between the pot life of the catalyzed mixture and the time at the end of which the molded article can be handled (these times depend on the targeted application such as, for example, the molding or manufacture of seals). In addition, the components that are reactive in the presence of the catalyst must confer, on the catalyzed mixture, a spreading time which does not vary as a function of the storage time.

Thus, when the organosilicon compound A is a polyorganosiloxane bearing at least two hydroxyl groups (of silanol type ≡SiOH), it has been discovered, surprisingly and unexpectedly, that when it is used in a composition according to the invention which comprises as catalyst a zinc complex bearing carboxylate and amine ligands according to the invention, it is then possible to increase or decrease the "working time" (or pot life) by simply varying the molar mass of the organosilicon compound A within a specific range. Thus, by varying the weight-average molar masses ($M_w$) of the organosilicon compound A within a range of values greater than at least twice the entanglement molar mass $M_e$, it is then possible to modify the "working time" (or pot life) without deteriorating the mechanical properties (for example the shore A hardness) of the elastomer obtained after crosslinking. Without being bound by theory, the formation of points of entanglement starting from a certain length of macromolecular chains for each type of polyorganosiloxane is thus possible starting from a certain entanglement molar mass of the polymer identified by the symbol "$M_e$". Thus, the "critical molar mass" noted $M_c$ is defined as being equal to about twice the entanglement molar mass $M_e$. Above the critical molar mass $M_c$, it was thus possible to control the "working time" (or pot life) of the silicone composition before crosslinking.

As a guide and depending on the type of group present in the polyorganosiloxane bearing at least two hydroxyl groups of silanol type ≡SiOH, the entanglement molar mass $M_e$ is between 15 000 and 30 000 g/mol.

Thus, an advantageous embodiment consists in using an organosilicon compound A which is a polyorganosiloxane bearing at least two hydroxyl groups of silanol type ≡SiOH whose weight-average molar mass $M_w$ is greater than at least twice the entanglement molar mass $M_e$. Controlling, by virtue of the choice of the weight-average molar mass Mw of the organosilicon compound A, the presence or absence of entanglement of the polyorganosiloxane chains bearing at least two hydroxyl groups of silanol type ≡SiOH makes it possible simultaneously to control:

the mechanical properties of the elastomer obtained after crosslinking of the composition according to the invention and especially the shore A hardness, and the "working time" during which the composition is manipulable before crosslinking.

Controlling the entanglement of the chains of the polyorganosiloxane bearing at least two hydroxyl groups of silanol type ≡SiOH will be performed by carefully selecting the weight-average molar mass $M_w$ of the polymer so that its molar mass is at least twice as large as the entanglement molar mass, i.e. it will be greater than the critical molar mass $M_c$ of this polymer.

Preferably, the organosilicon compound A is a polyorganosiloxane of general formula (6):

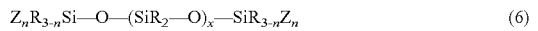

$$Z_n R_{3-n} Si\text{—}O\text{—}(SiR_2\text{—}O)_x\text{—}SiR_{3-n}Z_n \quad (6)$$

in which:

the symbols Z, which may be identical or different, each represent a hydrolyzable and condensable group or a hydroxyl group and are preferably chosen from the group consisting of groups of the following types: hydroxyl, alkoxy, alkoxy-alkylene-oxy, amino, amido, acylamino, aminoxy, iminoxy, ketiminoxy, acyloxy and enoxy, the symbols R, which may be identical or different, represent $C_1$ to $C_{30}$ monovalent hydrocarbon-based radicals optionally substituted with one or more halogen atoms or with amino, ether, ester, epoxy, mercapto or cyano groups, the symbol n is equal to 1, 2 or 3, preferably equal to 2 or 3 and when Z is a hydroxyl group, then n=1, the symbol x is between 200 and 10 000, preferably between 200 and 1000 and even more preferentially between 250 and 600.

In formulae (4), (5) and (6), the symbols $R^1$ and R are preferably:

alkyl radicals containing from 1 to 20 carbon atoms optionally substituted with: 1 or more aryl or cycloalkyl groups, with one or more halogen atoms or with amino, ether, ester, epoxy, mercapto, cyano or (poly)glycol groups. Examples that may be mentioned include methyl, ethyl, propyl, isopropyl, butyl, pentyl, hexyl, 2-ethylhexyl, octyl, decyl, 3,3,3-trifluoropropyl, 4,4,4-trifluorobutyl and 4,4,4,3,3-pentafluorobutyl radicals, cycloalkyl and halocycloalkyl radicals containing from 5 to 13 carbon atoms, such as cyclopentyl, cyclohexyl, methylcyclohexyl, propylcyclohexyl, 2,3-difluorocyclobutyl and 3,4-difluoro-5-methylcycloheptyl radicals, mononuclear aryl and haloaryl radicals containing from 6 to 13 carbon atoms, such as phenyl, tolyl, xylyl, chlorophenyl, dichlorophenyl or trichlorophenyl radicals, or alkenyl radicals containing from 2 to 8 carbon atoms, such as vinyl, allyl or 2-butenyl radicals.

The dynamic viscosity at 25° C. of the organosilicon compound A is generally between 50 and 5 000 000 mPa·s at 25° C. and preferably between 50 and 1 000 000 mPa·s. It is pointed out that the viscosity values in the present specification are the dynamic viscosity values measured at 25° C. using a Brookfield viscometer.

In the particular case where the organosilicon compound A is a polyorganosiloxane of general formula (6) with symbols Z of hydroxyl type, then the symbol n will preferably be equal to 1. In this case, it is preferred to use polydimethylsiloxanes with dimethylhydroxysilyl end groups, which are generally oils whose viscosity at 25° C. ranges, for example, between 100 mPa·s and 500 000 mPa·s or between 500 mPa·s and 200 000 mPa·s at 25° C. When it is desired to control the lifetime of the bath, for example, in a molding application, it will be arranged such that the choice of the organosilicon compound A is made as a function of the weight-average molar mass $M_w$ ($M_w$ greater than at least twice the entanglement molar mass $M_e$). For a molding application and when the compound is a polydimethylsiloxane ending with silanol functions (≡SiOH), its viscosity will preferably be greater than 750 mPa·s and even more preferentially between 1000 mPa·s and 20 000 mPa·s.

When the organosilicon compound A is a polyorganosiloxane, it is advantageous to use those in which at least 60% of the radicals R and $R^1$ (in formulae 4 and 5) or of the radical R (in formula 6) are methyl radicals, the other radicals generally being phenyl and/or vinyl radicals.

According to the invention, the symbols Z each represent a hydroxyl group or a hydrolyzable and condensable group which are preferably chosen from the group consisting of groups of the following types: alkoxy, alkoxy-alkylene-oxy, amino, amido, acylamino, aminoxy, iminoxy, ketiminoxy, acyloxy and enoxy, When the organosilicon compound A contains hydrolyzable and condensable groups Z according to the invention and is a polyorganosiloxane, it is usually described as a functionalized polymer and corresponds to a form that is stable in the absence of moisture which may be used in a one-pack composition and may thus be packaged in hermetically sealed cartridges, which will be opened by the operator during use to form, after curing, a cured elastomer. When the organosilicon group A contains groups Z of hydroxyl type, they may be functionalized in situ in the one-pack compositions, via a functionalization catalyst such as lithium hydroxide, so as to be able to store them and package them in hermetically sealed cartridges.

As examples of hydrolyzable and condensable groups Z of alkoxy type, mention may be made groups containing from 1 to 8 carbon atoms, such as methoxy, ethoxy, n-propoxy, isopropoxy, n-butoxy, isobutoxy, sec-butoxy, tert-butoxy, 2-methoxyethoxy, hexyloxy or octyloxy groups.

As an example of hydrolysable and condensable groups Z of alkoxy-alkylene-oxy type, mention may be made of the methoxy-ethylene-oxy group.

As examples of hydrolyzable and condensable groups Z of amino type, mention may be made of methylamino, dimethylamino, ethylamino, diethylamino, n-butylamino, sec-butylamino or cyclohexylamino groups.

As an example of hydrolyzable and condensable groups Z of amido type, mention may be made of the N-methylacetamido group.

As an example of hydrolyzable and condensable groups Z of acylamino type, mention may be made of the benzoylamino group.

As examples of hydrolyzable and condensable aminoxy groups Z, mention may be made of dimethylaminoxy, diethylaminoxy, dioctylaminoxy or diphenylaminoxy groups.

As examples of hydrolyzable and condensable groups Z of iminoxy and in particular ketiminoxy type, mention may be made of groups derived from the following oximes: acetophenone oxime, acetone oxime, benzophenone oxime, methylethylketoxime, diisopropylketoxime or methylisobutylketoxime.

As an example of hydrolysable and condensable groups Z of acyloxy type, mention may be made of the acetoxy group.

As an example of hydrolyzable and condensable groups Z of enoxy type, mention may be made of the 2-propenoxy group.

The crosslinking agent B is preferably a silicon compound, each molecule of which comprises at least three hydrolyzable and condensible groups Y and said crosslinking agent B having formula (7) below:

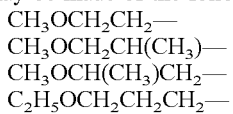
(7)

in which formula:
the symbol R' is a monovalent hydrocarbon-based radical comprising from 1 to 30 carbon atoms,
the symbol Y is an alkoxy, alkoxy-alkylene-oxy, amino, amido, acylamino, aminoxy, iminoxy, ketiminoxy, acyloxy or enoxy group and preferably Y is an alkoxy, acyloxy, enoxy, ketiminoxy or oxime group, the symbol a=3 or 4.

Examples of groups Y are the same as those mentioned above when the symbol Z is a hydrolyzable and condensable group, i.e. other than a hydroxyl group.

As examples of crosslinking agent B, mention may be made of the alkoxysilanes of general formula (8) below, and the products of partial hydrolysis of this silane:

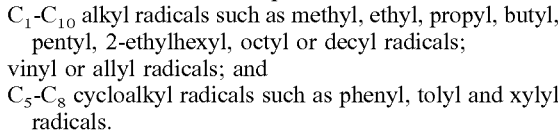
(8)

in which:
the symbols $R^2$, which may be identical or different, represent alkyl radicals containing from 1 to 8 carbon atoms, such as methyl, ethyl, propyl, butyl, pentyl, 2-ethylhexyl radicals or $C_3$-$C_6$ oxyalkylene radicals,
the symbol $R^3$ represents a saturated or unsaturated, linear or branched aliphatic hydrocarbon-based group, a saturated or unsaturated and/or aromatic monocyclic or polycyclic carbocyclic group,
k is equal to 0, 1 or 2.

As examples of $C_3$-$C_6$ alkoxyalkylene radicals, mention may be made of the following radicals:
$CH_3OCH_2CH_2$—
$CH_3OCH_2CH(CH_3)$—
$CH_3OCH(CH_3)CH_2$—
$C_2H_5OCH_2CH_2CH_2$—

The symbol $R^3$ preferably represents a $C_1$-$C_{10}$ hydrocarbon-based radical that encompasses:
$C_1$-$C_{10}$ alkyl radicals such as methyl, ethyl, propyl, butyl, pentyl, 2-ethylhexyl, octyl or decyl radicals;
vinyl or allyl radicals; and
$C_5$-$C_8$ cycloalkyl radicals such as phenyl, tolyl and xylyl radicals.

These crosslinking agents B are products that are available on the silicones market; furthermore, their use in room-temperature curing compositions is known; it is featured especially in French patents FR-A-1 126 411, FR-A-1 179 969, FR-A-1 189 216, FR-A-1 198 749, FR-A-1 248 826, FR-A-1 314 649, FR-A-1 423 477, FR-A-1 432 799 and FR-A-2 067 636.

Among the crosslinking agents B, preference is more particularly given to alkyltrialkoxysilanes, alkyl silicates and polyalkyl silicates, in which the organic radicals are alkyl radicals containing from 1 to 4 carbon atoms.

As other examples of crosslinking agents B that may be used, mention may be made more particularly of polyethyl silicate, poly(n-propyl silicate) and the following silanes: propyltrimethoxysilane, methyltrimethoxysilane, ethyltrimethoxysilane, vinyltriethoxysilane, vinyltrimethoxysilane, methyltriethoxysilane, propyltriethoxysilane, tetramethoxysilane, tetraethoxysilane, tetrapropoxysilane, tetrabutoxysilane 1,2-bis(trimethoxysilyl)ethane, 1,2-bis(triethoxysilyl)ethane, tetraisopropoxysilane, phenyltriethoxysilane, methyltris(methylethylketoximo)silane, 3-cyanopropyltrimethoxysilane, 3-cyanopropyltriethoxysilane, 3-(glycidyloxy)propyltriethoxysilane, vinyltris(methylethylketoximo)silane, tetrakis(methylethylketoximo)silane, acyloxysilanes such as vinyltriacetoxysilane, methyltriacetoxysilane or ethyltriacetoxysilane or alternatively those having the following formulae:

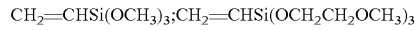

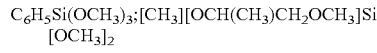

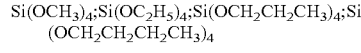

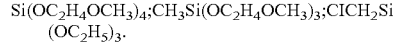

Use is generally made of 0.1 to 60 parts by weight of crosslinking agent B per 100 parts by weight of organosilicon compound A. Preferably, use is made of 1 to 15 parts by weight per 100 parts by weight of organosilicon compound A.

As fillers C, use may be made of mineral fillers that are very finely divided products with a mean particle diameter of less than 0.1 μm. The fillers C, preferably reinforcing silicas, are generally used in a proportion of from 1 to 150 parts and preferably from 8 to 100 parts per 100 parts of organosilicon compound A. They are chosen from combustion silicas and precipitation silicas. They have a specific surface area, measured according to the BET and CTAB methods, of at least 50 m²/g and preferably greater than 70 m²/g, a mean primary particle size of less than 80 nm and an apparent density of less than 200 g/liter. These silicas may be incorporated in unmodified form or after having been treated with organosilicon compounds usually used for this purpose. Among these compounds are methylpolysiloxanes such as hexamethyldisiloxane, hexamethylcyclotetrasiloxane, methylpolysilazanes such as hexamethyldisilazane, hexamethylcyclotrisilazane, chlorosilanes such as dimethyldichlorosilane, trimethylchlorosilane, methylvinyldichlorosilane, dimethylvinylchlorosilane, alkoxysilanes such as dimethyldimethoxysilane, dimethylvinylethoxysilane, trimethylmethoxysilane.

In addition to or instead of the reinforcing silicas, semi-reinforcing or bulking mineral fillers may be added. These fillers are coarser and have a mean particle diameter of greater than 0.1 µm. These fillers are more especially represented by ground quartz, calcined clays, diatomaceous silicas, calcium carbonate, iron oxide, titanium oxide, magnesium oxide, aluminum oxide, zinc sulfate and barium sulfate. They are generally introduced in a proportion of from 1 to 120 parts by weight per 100 parts of organosilicon compound A. These mineral fillers may be used in unmodified form, i.e. untreated, or treated with the organosilicon compounds mentioned above in the case of the reinforcing silicas.

The purpose of introducing fillers is to give good rheological properties to the composition before crosslinking and good mechanical properties to the elastomers that result from the curing of the compositions in accordance with the invention.

In combination with these fillers, use may be made of mineral and/or organic pigments and also agents that improve the thermal resistance (salts and oxides of rare-earth elements such as ceric oxides and hydroxides) and/or the fire resistance of the elastomers. For example, the oxide cocktails described in international application WO 98/29488 can be used. Among the agents that improve the fire resistance, mention may be made of halogenated organic derivatives, organophosphorus derivatives, platinum derivatives such as chloroplatinic acid (its products from reaction with alkanols, ether oxides), and platinous chloride-olefin complexes. These pigments and agents together represent at most 20% of the weight of the fillers.

The composition according to the invention may also comprise at least one adhesion promoter E, for instance organosilicon compounds bearing both:
(1) one or more hydrolyzable groups bonded to the silicon atom, and
(2) one or more organic groups substituted with radicals comprising a nitrogen atom or chosen from the group of (meth)acrylate, epoxy and alkenyl radicals, and more preferably still from the group constituted by the following compounds, taken alone or as a mixture:
vinyltrimethoxysilane (VTMO);
3-glycidoxypropyltrimethoxysilane (GLYMO);
methacryloxypropyltrimethoxysilane (MEMO);
[H$_2$N(CH$_2$)$_3$]Si(OCH$_2$CH$_3$)$_3$;
[H$_2$N(CH$_2$)$_3$]Si(OCH$_3$)$_3$;
[H$_2$N(CH$_2$)$_3$]Si(OC$_2$H$_5$)$_3$;
[H$_2$N(CH$_2$)$_4$]Si(OCH$_3$)$_3$;
[H$_2$NCH$_2$CH(CH$_3$)CH$_2$CH$_2$]SiCH$_3$(OCH$_3$)$_2$,
[H$_2$NCH$_2$]Si(OCH$_3$)$_3$;
[-n-C$_4$H$_9$—HN—CH$_2$]Si(OCH$_3$)$_3$;
[H$_2$N(CH$_2$)$_2$NH(CH$_2$)$_3$]Si(OCH$_3$)$_3$;
[H$_2$N(CH$_2$)$_2$NH(CH$_2$)$_3$]Si(OCH$_2$CH$_2$OCH$_3$)$_3$;
[CH$_3$NH(CH$_2$)$_2$NH(CH$_2$)$_3$]Si(OCH$_3$)$_3$;
[H$_2$N(NHCH$_2$CH$_2$)$_2$NH(CH$_2$)$_3$]Si(OCH$_3$)$_3$,

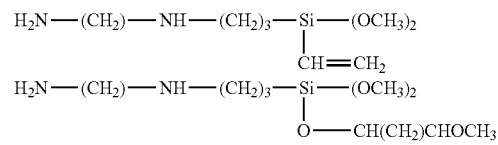

or polyorganosiloxane oligomers containing such organic groups in a content of greater than 20%.

Besides the main constituents, nonreactive linear polyorganosiloxane polymers (G) may be introduced with the intention of acting on the physical characteristics of the compositions in accordance with the invention and/or on the mechanical properties of the elastomers resulting from the curing of these compositions.

These nonreactive linear polyorganosiloxane polymers (G) are well known; they more especially comprise: α,ω-bis(triorganosiloxy)diorganopolysiloxane polymers with viscosities of at least 10 mPa·s at 25° C., formed essentially from diorganosiloxy units and from at most 1% of monoorganosiloxy and/or siloxy units, the organic radicals bonded to the silicon atoms being chosen from methyl, vinyl and phenyl radicals, 60% at least of these organic radicals being methyl radicals and 10% at most being vinyl radicals. The viscosity of these polymers can reach several tens of millions of mPa·s at 25° C.; they therefore include oils with a fluid to viscous appearance and soft to hard gums. They are prepared according to the usual techniques described more precisely in French patents FR-A-978 058, FR-A-1 025 150, FR-A-1 108 764 and FR-A-1 370 884. Use is preferably made of α,ω-bis(trimethylsiloxy)dimethylpolysiloxane oils with a viscosity ranging from 10 mPa·s to 1000 mPa·s at 25° C. These polymers, which act as plasticizers, may be introduced in a proportion of at most 70 parts by weight, preferably of 5 to 20 parts, per 100 parts of the organosilicon compound A.

The compositions according to the invention may moreover advantageously comprise at least one silicone resin (H). These silicone resins are branched organopolysiloxane polymers which are well known and which are available commercially. They have, per molecule, at least two different units chosen from those of formula R'''$_3$SiO$_{1/2}$ (M unit), R'''$_2$SiO$_{2/2}$ (D unit), R'''SiO$_{3/2}$ (T unit) and SiO$_{4/2}$ (Q unit) with at least one of the units being a T or Q unit. The R''' radicals are identical or different and are chosen from linear or branched alkyl radicals or vinyl, phenyl or 3,3,3-trifluoropropyl radicals. Preferably, the alkyl radicals have from 1 to 6 carbon atoms inclusive. More particularly, mention may be made, as examples of alkyl R radicals, of methyl, ethyl, isopropyl, tert-butyl and n-hexyl radicals. These resins are preferably hydroxylated and, in this case, have a weight content of hydroxyl group of between 5 and 500 meq./100 g. Examples of resins that may be mentioned include MQ resins, MDQ resins, TD resins and MDT resins.

Other customary auxiliary agents and additives may be incorporated into the composition according to the invention; these are chosen as a function of the applications in which said compositions are used.

The composition according to the invention may comprise the following amounts:
per 100 parts by weight of at least one organosilicon compound A comprising at least two identical or different hydrolyzable and condensable groups, or at least two silanol functions ≡SiOH,
from 0.1 to 60 parts by weight, preferably from 1 to 15 parts by weight, of at least one crosslinking agent B, from 0 to 150 parts by weight of at least one filler C,
from 0 to 20 parts by weight of at least one adhesion promoter E,
from 0 to 150 parts by weight of at least one nonreactive linear polyorganosiloxane polymer G,
from 0 to 50 parts by weight of at least one silicone resin H, and
a catalytically effective amount of at least one polycondensation catalyst M according to the invention.

According to one variant of the invention, the composition according to the invention does not contain any catalyst containing at least one tin atom in its structure.

According to another variant of the invention, the polycondensation catalyst M is the only polycondensation catalyst present in said composition, which may optionally contain at least one functionalization catalyst.

Another subject of the invention relates to an RTV-2 two-pack composition, the precursor of the composition according to the invention and as described above, which is in two distinct packages P1 and P2, characterized in that:
the package P1, which is airtight, comprises:
a catalytically effective amount of at least one polycondensation catalyst M as defined above, and
at least one crosslinking agent B, and
the package P2 does not contain said polycondensation catalyst M and said crosslinking agent B and comprises:
per 100 parts by weight of at least one organosilicon compound A as defined above, and
from 0 to 10 part(s) by weight of water.

According to an advantageous embodiment, it has been discovered that, in molding applications, and for an RTV-2 two-pack composition according to the invention comprising at least one catalyst according to the invention combined with an α,ω-dihydroxylated polydimethylsiloxane oil as organosilicon compound A, it is then possible to modify the lifetime of the bath, after mixing the contents P1 and P2 just before use, by simply varying the viscosity of the α,ω-dihydroxylated polydimethylsiloxane oil chosen while at the same time choosing an oil with a molecular mass $M_w$ greater than at least twice the critical entanglement molar mass $M_c$ of this polymer.

Thus, it has been discovered that by combining a catalyst according to the invention associated with at least one α,ω-dihydroxylated polydimethylsiloxane oil whose viscosity is between 2000 mPa·s and 5000 mPa·s, and preferably between 3000 and 4000 mPa·s, it is then possible to increase the working time when the parts P1 and P2 are combined just before use in a molding application, without deteriorating the hardness properties when the composition is hardened after crosslinking (Shore A hardness, SAH at 24 hours and at 4 days). Thus, according to a preferred embodiment, the invention relates to an RTV-2 two-pack composition for a molding application, the precursor of the composition as defined above, which is in two separate packages P1 which is airtight and P2, characterized in that:
the package P1 comprises:
a catalytically effective amount of at least one polycondensation catalyst M according to the invention and as defined above, and
at least one crosslinking agent B preferably as defined above, and
the package P2 does not contain said polycondensation catalyst M and said crosslinking agent B and comprises:
per 100 parts by weight of at least one organosilicon compound A which is an α,ω-bis(dimethylhydroxysilyl)polydimethylsiloxane whose dynamic viscosity at 25° C. is between 2000 mPa·s and 5000 mPa·s and preferably between 3000 mPa·s and 4000 mPa·s, and
from 0 to 10 part(s) by weight of water.

One of the advantages of these novel RTV-2 compositions according to the invention over conventional polycondensation RTV-2 products using dialkyltin dicarboxylate catalysts is that it is no longer necessary to add water to the part P2 since the catalyst according to the invention does not need to be activated, thus simplifying the formulation.

Another subject of the invention relates to an RTV-1 one-pack composition which is in a single airtight package P, comprising:
a) at least one organosilicon compound A comprising at least two identical or different hydrolyzable and condensable groups, or at least two silanol functions ≡SiOH,
b) at least one crosslinking agent B, and
c) a catalytically effective amount of at least one polycondensation catalyst M, and
d) optionally at least one filler C.

For the RTV-1 one-pack composition or RTV-2 two-pack composition, other components may be present, such as: the adhesion promoter E, the nonreactive linear polyorganosiloxane polymer G, the silicone resin H and the other additives as described in the present specification.

An RTV-2 two-pack composition is in two separate packages P1, which contains the catalyst and is airtight, and P2. They are packaged, after incorporation of the catalyst, in two separate fractions, one of the fractions possibly containing, for example, only the catalyst according to the invention or a mixture with the crosslinking agent. The manufacture of the RTV-2 two-pack compositions in accordance with the invention is also performed by mixing the various constituents in suitable equipment. RTV-2 two-pack compositions are described in detail, for example, in patents EP 118 325, EP 117 772, EP 10 478, EP 50 358, EP 184 966, U.S. Pat. No. 3,801,572 and U.S. Pat. No. 3,888,815 cited as reference.

An RTV-1 one-pack composition is in a single airtight package P that is stable on storage in the absence of moisture, which can be cured in the presence of moisture, in particular moisture provided by the ambient air or by water generated within the base during the use thereof. In order to manufacture the compositions according to the invention it is preferable, in the case of the one-pack compositions, to use equipment that makes it possible to intimately mix the various fundamental constituents in a moisture-free environment, with or without a supply of heat, optionally added to which constituents are the aforementioned adjuvants and additives. All these ingredients may be loaded into the equipment in any order of introduction. Thus, it is possible first to mix the organosilicon compound A and the fillers C and then to add to the slurry obtained the crosslinking agent B, and optionally the other components when they are present and finally the polycondensation catalyst M according to the invention. It is also possible to mix the organosilicon compound A, the crosslinking agent B, the filler C and optionally the other components and subsequently to add the polycondensation catalyst M according to the invention. During these operations, the mixtures may be heated to a temperature from 50° C. to 180° C. at atmospheric pressure or under a reduced pressure in order to promote the removal of volatile materials. The RTV-1 one-pack compositions in accordance with the invention are used in unmodified form, i.e. undiluted, or in the form of dispersions in diluents, and are stable on storage in the absence of moisture or water and cure at low temperatures (after removal of the solvents in the case of dispersions) in the presence of water to form elastomers. RTV-1 one-pack compositions are described in detail, for example, in patents EP 141 685, EP 147 323, EP 102 268, EP 21 859, FR 2 121 289 and FR 2 121 631, cited as reference.

After the deposition in unmodified form of the compositions according to the invention prepared from an RTV-1 one-pack composition, onto solid substrates, in a humid atmosphere, it is observed that a process of curing into elastomers occurs, it takes place from the outside to the inside of the mass deposited. A skin forms first at the surface, then the crosslinking continues in depth. The complete formation of the skin, which results in a tack-free feel of the surface, requires a period of time of a few minutes; this period of time depends on the degree of relative humidity of the atmosphere surrounding the compositions and on the crosslinkability of the latter.

Furthermore, the in-depth curing of the deposited layers, which must be sufficient to allow the demolding and handling of the elastomers formed, requires a longer period of time. Indeed, this period of time depends not only on the factors mentioned above for the formation of the tack-free feel but also on the thickness of the deposited layers, which thickness generally lies between 0.5 mm and several centimeters. The one-pack compositions may be used for multiple applications such as jointing in the construction industry, assembling the most diverse materials (metals, plastics, natural and synthetic rubbers, wood, board, earthenware, brick, ceramic, glass, stone, concrete, masonry units), insulating electrical conductors, the potting of electronic circuits, or the preparation of molds used for manufacturing articles made of synthetic resins or foams.

The compositions in accordance with the invention may be used for multiple applications such as jointing and/or bonding in the construction industry, in the transport industry (examples: motor vehicle, aerospace, railway, maritime and aeronautical), assembling the most diverse materials (metals, plastics, natural and synthetic rubbers, wood, cardboard, polycarbonate, earthenware, brick, ceramic, glass, stone, concrete and masonry units), insulating electrical conductors, the potting of electronic circuits, and the preparation of molds used for manufacturing articles made of synthetic resins or foams.

It is possible to add, to these one-pack bases, adhesion promoters E chosen, for example, from organosilicon compounds simultaneously bearing, on the one hand, organic groups substituted by radicals chosen from the group of amino, ureido, isocyanate, epoxy, alkenyl, isocyanurate, hydantoyl, guanidino and mercaptoester radicals and, on the other hand, hydrolyzable groups, in general alkoxy groups bonded to the silicon atoms. Examples of such adhesion agents are described in United States patents U.S. Pat. No. 3,517,001, U.S. Pat. No. 4,115,356, U.S. Pat. No. 4,180,642, U.S. Pat. No. 4,273,698, U.S. Pat. No. 4,356,116 and in European patents EP 31 996 and EP 74 001.

The compositions according to the invention are particularly useful for molding applications, in particular when they are in the RTV-2 two-pack form. For the use of the compositions according to the invention in this application, the techniques of casting or of application via a spatula or a brush or by spraying are useful.

Examples of molding techniques that may be mentioned include:
"box molding", which is intended for the manufacture of self-supporting molds, in one or more parts, by simple casting of the composition after mixing the two parts of the RTV-2 in liquid form on the initial master cast. This process is preferred for relatively simple forms without substantial reverse tapers;
"molding in encasing in one or two parts", and
"compression molding", which is preferred for making an imprint of inclined, vertical or overhanging master casts, generally of large size or when it is impossible to move the master cast.

Another subject of the invention relates to an elastomer obtained:
after mixing the contents of the packages P1 and P2 of the RTV-2 two-pack composition according to the invention and as described above and leaving the mixture to cure,
after placing in contact with atmospheric moisture the contents of the package P of the RTV-1 one-pack composition according to the invention and as described above and leaving said contents to cure, or
after preparing the composition according to the invention and as described above and leaving the mixture to cure in the presence of water or of atmospheric moisture.

Another subject of the invention relates to a process for coating the composition according to the invention and as defined above onto a flexible support S which is made of textile, paper, polyvinyl chloride, polyester, polypropylene, polyamide; polyethylene; polyurethane or polyethylene terephthalate, comprising steps a), b) and c) below:
a) a composition according to the invention and as defined above is prepared,
b) said composition is then deposited in continuous or batch manner onto said flexible support S, and
c) said silicone composition X is left to crosslink in the presence of moisture provided by the ambient air or by prior addition of water so as to form a silicone elastomer.

The coating of silicone compositions according to the invention onto flexible supports targets numerous applications. For example, when the flexible support is a textile, water-repellency properties are sought, or, when the support is a paper or a polymer such as PVC, PET, etc., non-stick properties are usually sought.

Thus, once applied to a support, the silicone composition according to the invention crosslinks by means of the atmospheric moisture and/or by the presence of water in the composition to form a solid coating of silicone elastomer. In these liquid silicone coating compositions, the silicone phase may be diluted in a solvent.

According to one variant of the process according to the invention, the composition in step a) is prepared after mixing the contents of the packages P1 and P2 of the RTV-2 two-pack composition according to the invention and as defined above or using the contents of the package P of the RTV-1 one-pack composition according to the invention and as defined above.

The flexible supports S coated with a non-stick silicone film or with a non-stick silicone coat cured by crosslinking are chosen from the group consisting of supports made of textile, paper, polyvinyl chloride, polyester, polypropylene, polyamide; polyethylene; polyurethane or polyethylene terephthalate.

For the purposes of the invention, the term "textile" is a generic term including all textile structures. The textiles may consist of yarns, fibers, filaments and/or other materials. They especially comprise flexible fabrics, whether they are woven, bonded, knitted, plaited, felted, needled, sewn, or made via another manufacturing method.

The textiles may be openwork, i.e. they may comprise open spaces not comprising any textile. In order for the coating of the silicone composition of the invention to be efficient, it is preferable for the smallest of the dimensions of these open spaces to be less than 5 mm and especially less than 1 mm.

According to the invention, any type of flexible textile support S may be used. As a guide, mention may be made of:
  natural textile fibers, such as: textiles of vegetable origin, such as cotton, flax, hemp, jute, coconut, paper cellulose fibers; and textiles of animal origin, such as wool, furs, leather and silks;
  artificial textiles, such as: cellulose-based textiles, such as cellulose or derivatives thereof; and protein-based textiles of animal or vegetable origin; and
  synthetic textiles, such as polyester, polyamide, polymalic alcohols, polyvinyl chloride, polyacrylonitrile, polyolefins, acrylonitrile, (meth)acrylate-butadiene-styrene copolymers and polyurethane.

The synthetic textiles obtained by polymerization or polycondensation may especially comprise in their matrix various types of additives, such as pigments, delustering agents, matt-effect agents, catalysts, heat and/or light stabilizers, antistatic agents, flame retardants, and antibacterial, antifungal and/or antiacarian agents.

As flexible textile types of support, mention may be made especially of supports obtained by rectilinear entanglement of yarns or fabrics, supports obtained by curvilinear interlacing of yarns or knits, mixtilinear surfaces or tulles, nonwoven supports and composite supports. Among the multitude of possible textile supports that may be used in the process of the invention, mention may be made of felts, denims, jacquard wovens, needled fabrics, sewn fabrics, crocheted fabrics, grenadines, laces and laceworks, damasks, webs, alpacas, baratheas, dimity fabrics, loop fabrics, brocades, calicos, velvets, canvasses, chiffons, flocked fabrics, sized fabrics, cheese-cloths, plaited fabrics, failles, foulard fabrics, gauzes, geotextiles, grandrelles, cushioned fabrics, tufted fabrics, organzas, pleated fabrics, ribbons and toiles.

The flexible textile support S used in the process of the present invention may consist of one or more identical or different textiles, assembled in various ways. The textile may be a monolayer or multilayer textile. The textile support may consist, for example, of a multilayer structure which may be made via various assembly means, such as mechanical means, for instance sewing, welding, or spot or continuous bonding.

The flexible textile support S may undergo, besides the coating process according to the present invention, one or more other subsequent treatments, also known as finishing or dry-filling treatments. These other treatments may be performed before, after and/or during said coating process of the invention. As other subsequent treatments, mention may be made especially of: dyeing, printing, back-bonding, coating, assembly with other materials or textile surfaces, washing, degreasing, preforming or fixing.

According to a preferred embodiment of the invention, the flexible textile support S is a lace or an elastic band.

The textiles thus obtained, in unmodified form or transformed into textile articles, may be used in numerous applications, for instance in the field of clothing, especially lingerie such as lace stocking tops or bra lacing, and hygiene articles, such as strapping tapes or dressings. These textile articles may be repositioned in various places of the body or of an item of clothing, for example by means of the adherence provided by the silicone elastomer.

In practice, the rate of deposition of the composition according to the invention onto the flexible support S is between 0.1 and 1 and preferably between 0.3 and 0.5 g/m$^2$, which corresponds to thicknesses of the order of a micrometer.

Another subject of the invention relates to the use of a polycondensation catalyst M according to the invention and as defined above as a catalyst for the polycondensation reaction of a silicon compound comprising at least two identical or different hydrolyzable and condensable groups, or at least two silanol functions ≡SiOH.

Finally, the last subject of the invention relates to complexes having the following formulae:
[Zn(naphthenate)$_2$ (bis(2-ethylhexyl)amine)],
[Zn(naphthenate)$_2$ (bis(2-ethylhexyl)amine)$_2$],
[Zn(naphthenate)$_2$ (diisononylamine)],
[Zn(naphthenate)$_2$ (diisononylamine)$_2$],
[Zn(naphthenate)$_2$ (di(n-octyl)amine)],
[Zn(naphthenate)$_2$ (di(n-octyl)amine)$_2$],
[Zn(naphthenate)$_2$(n-octylamine)],
[Zn(naphthenate)$_2$(n-octylamine)$_2$],
[Zn(naphthenate)$_2$(N,N-dibutylamine)],
[Zn(naphthenate)$_2$(N,N-dibutylamine)$_2$],
[Zn(naphthenate)$_2$(N,N-dimethyl-N-butylamine)$_2$],
[Zn(naphthenate)$_2$(N,N-dimethyl-N-butylamine)$_2$],
[Zn(neodecanoate)$_2$(di(n-octyl)amine)],
[Zn(neodecanoate)$_2$(di(n-octyl)amine)]$_2$],
[Zn(neodecanoate)$_2$(n-octylamine)],
[Zn(neodecanoate)$_2$(n-octylamine)$_2$],
[Zn(neodecanoate)$_2$(N,N-dibutylamine)],
[Zn(neodecanoate)$_2$(N,N-dibutylamine)$_2$],
[Zn(neodecanoate)$_2$(3-aminopropyltrimethoxysilane)$_2$],
[Zn(neodecanoate)$_2$ (3-aminopropylmethyldiethoxysilane)$_2$],
[Zn(neodecanoate)$_2$ (bis(2-ethylhexyl)amine)],
[Zn(neodecanoate)$_2$ (bis(2-ethylhexyl)amine)$_2$],
[Zn(neodecanoate)$_2$ (diisononylamine)],
[Zn(neodecanoate)$_2$ (diisononylamine)$_2$],
[Zn(2-ethylhexanoate)$_2$(N,N-dibutylamine)]
[Zn(2-ethylhexanoate)$_2$(N,N-dibutylamine)$_2$],
[Zn(2-ethylhexanoate)$_2$(n-octylamine)],
[Zn(2-ethylhexanoate)$_2$(n-octylamine)$_2$],
[Zn(2-ethylhexanoate)$_2$ (bis(2-ethylhexyl)amine)],
[Zn(2-ethylhexanoate)$_2$ (bis(2-ethylhexyl)amine)$_2$],
[Zn(2-ethylhexanoate)$_2$ (diisononylamine)], and
[Zn(2-ethylhexanoate)$_2$ (diisononylamine)$_2$].

Other advantages and features of the present invention will appear on reading the following examples that are given by way of illustration and that are in no way limiting.

EXAMPLES

Example 1

Preparation of the [Zn(Carboxylate)$_2$(Amine)$_n$] Complexes a) Preparation of the Complexes [Zn(2-Ethylhexanoate)$_2$ (Amine)$_n$], [Zn(Naphthenate)$_2$(Amine)$_n$] and [Zn(Neodecanoate)$_2$(Amine)$_n$]

To a solution of 121.1 g of neodecanoic acid (0.7 mol) or 165.9 g of naphthenic acid or 102 g of 2-ethyl hexanoic acid at 99% in 300 g of toluene are added over 1 hour 125.44 g of a solution of sodium methoxide at 30.1% by weight in methanol (0.7 mol). Next, a solution of zinc chloride in slight excess (49.92 g at 98% by weight, 0.359 mol) in 50 g of methanol is added over 40 minutes. The methanol/toluene azeotrope is distilled off for 2 hours. The reaction mixture is cooled to room temperature and the sodium chloride is then filtered off. The clear, colourless solution is evaporated to dryness (at 70° C., 1 mbar) to give a viscous oil: 143.3 g of zinc neodecanoate or 229.2 g of zinc naphthenate or 123.2 g of zinc 2-ethylhexanoate (100% yield).

The amines (n-octylamine, di(n-octyl)amine), N,N-dibutylamine, bis(2-ethylhexyl)amine, diisononylamine, N,N-dimethyl-N-butylamine, 3-aminopropyltrimethoxysilane, aminoethylaminopropyltrimethoxysilane, aminopropyltriethoxysilane or 3-aminopropylmethyldiethoxysilane are added without solvent with vigorous stirring to the zinc carboxylates at the desired stoichiometry (either at least two molar equivalents of amine when it is desired predominantly to prepare a diamino zinc dicarboxylate complex, or between 1 and 2 equivalents when it is desired to prepare a monoamino or diamino mixture of the corresponding zinc dicarboxylate complexes, or close to 1 equivalent when it is desired predominantly to prepare the corresponding monoamino zinc dicarboxylate complex).

The desired complexes are obtained in sparingly viscous liquid form. The complexation reaction is exothermic. A solvent that is compatible with the application may be used to dilute the zinc carboxylate, such as heavy petroleum fractions, or mixtures of alkanes and/or of alkylaromatics. However, it is noted that it is preferable to add the amine directly to the zinc complex without the presence of other compounds or polymers that might bear functions that are reactive with one of the reagents.

Depending on the carboxylates, the nature of the amines and the amounts of amine added, the following complexes are obtained:

[Zn(naphthenate)$_2$ (bis(2-ethylhexyl)amine)],
[Zn(naphthenate)$_2$ (bis(2-ethylhexyl)amine)$_2$],
[Zn(naphthenate)$_2$ (diisononylamine)],
[Zn(naphthenate)$_2$ (diisononylamine)$_2$],
[Zn(naphthenate)$_2$ (di(n-octyl)amine)],
[Zn(naphthenate)$_2$ (di(n-octyl)amine)$_2$],
[Zn(naphthenate)$_2$(n-octylamine)],
[Zn(naphthenate)$_2$(n-octylamine)$_2$],
[Zn(naphthenate)$_2$(N,N-dibutylamine)],
[Zn(naphthenate)$_2$(N,N-dibutylamine)$_2$],
[Zn(naphthenate)$_2$(N,N-dimethyl-N-butylamine)$_2$],
[Zn(naphthenate)$_2$(N,N-dimethyl-N-butylamine)$_2$],
[Zn(naphthenate)$_2$(aminoethylaminopropyltrimethoxysilane)],
[Zn(naphthenate)$_2$(aminoethylaminopropyltrimethoxysilane)$_2$],
[Zn(naphthenate)$_2$(aminopropyltriethoxysilane)],
[Zn(naphthenate)$_2$(aminopropyltriethoxysilane)$_2$],
[Zn(neodecanoate)$_2$(di(n-octyl)amine)],
[Zn(neodecanoate)$_2$(di(n-octyl)amine)]$_2$],
[Zn(neodecanoate)$_2$(n-octylamine)],
[Zn(neodecanoate)$_2$(n-octylamine)$_2$],
[Zn(neodecanoate)$_2$(N,N-dibutylamine)],
[Zn(neodecanoate)$_2$(N,N-dibutylamine)$_2$],
[Zn(neodecanoate)$_2$(3-aminopropyltrimethoxysilane)$_2$],
[Zn(neodecanoate)$_2$ (3-aminopropylmethyldiethoxysilane)$_2$],
[Zn(neodecanoate)$_2$ (aminoethylaminopropyltrimethoxysilane)],
[Zn(neodecanoate)$_2$ (aminoethylaminopropyltrimethoxysilane)$_2$],
[Zn(neodecanoate)$_2$ (aminopropyltriethoxysilane)],
[Zn(neodecanoate)$_2$ (aminopropyltriethoxysilane)$_2$],
[Zn(neodecanoate)$_2$ (bis(2-ethylhexyl)amine)],
[Zn(neodecanoate)$_2$ (bis(2-ethylhexyl)amine)$_2$],
[Zn(neodecanoate)$_2$ (diisononylamine)],
[Zn(neodecanoate)$_2$ (diisononylamine)$_2$],
[Zn(2-ethylhexanoate)$_2$(N,N-dibutylamine)]
[Zn(2-ethylhexanoate)$_2$(N,N-dibutylamine)$_2$],
[Zn(2-ethylhexanoate)$_2$(n-octylamine)],
[Zn(2-ethylhexanoate)$_2$(n-octylamine)$_2$],
[Zn(2-ethylhexanoate)$_2$ (bis(2-ethylhexyl)amine)],
[Zn(2-ethylhexanoate)$_2$ (bis(2-ethylhexyl)amine)$_2$],
[Zn(2-ethylhexanoate)$_2$ (diisononylamine)], and
[Zn(2-ethylhexanoate)$_2$ (diisononylamine)$_2$].

The abbreviations for the ligands listed in the formulae of the tables below are as follows:
neodecanoate=ND
naphthenate=NAPH
n-octylamine=OA
di(n-octyl)amine=DOA
N,N-dibutylamine=DBA
N,N-dimethyl-N-butylamine=DMBA In the case where, during the synthesis, a variable amount of amine is used (>0 equivalent and ≤2 equivalents, or a slight excess), a mixture is obtained comprising the complexes: [Zn(carboxylate)$_2$(amine)]+[Zn(carboxylate)$_2$ (amine)$_2$]. The following nomenclature will then be used in this case: [Zn(carboxylate)$_2$ (amine)$_x$]* and the value of the symbol "x" refers to the number of moles of amine added during the preparation of the complex relative to the zinc and which have reacted (i.e. which are present in the complex as ligand). This type of nomenclature will be identified in the examples by insertion of the symbol "*" into the formula of the complex.

All the structures were confirmed by $^1$H NMR analysis in CDCl$_3$ solvent.

Example 2

RTV-2 Two-Pack Composition—Polyethyl Silicate Crosslinking Agent (a1): hydroxylated polydimethylsiloxane oil with a viscosity of 14 000 mPa·s at 25° C. and blocked at each of the chain ends with a siloxyl unit M$^{OH}$ having the following formula: (CH$_3$)$_2$(OH)SiO$_{1/2}$, (b1): fumed silica with a BET specific surface area of 200 m$^2$/g, treated with hexamethyldisilazane (HMDZ), dispersed in a mixture of hydroxylated polydimethylsiloxane oil (a1) and of a polydimethylsiloxane oil blocked at each of the chain ends with a siloxyl unit M having the following formula (CH$_3$)$_3$SiO$_{1/2}$;

(b2): ground quartz with a mean particle diameter of 10 μm;

(d1): catalyst tested;

(e): polyethyl silicate.

The activity of the catalysts according to the invention is evaluated relative to
the usual catalyst [Comparative: Fomrez® catalyst UL-28=dimethylbis[(1-oxoneodecyl)oxy]stannane, of formula [C$_9$H$_{19}$COO]$_2$Sn(Me)$_2$], and
the respective [Zn(carboxylate)$_2$] catalysts.

To do this, a slurry is prepared from the following constituents:
20.4 g of an α,ω-bis(hydroxydimethylsilyl)polydimethylsiloxane oil (a1),
61.3 g of a filler (b1), and
18.3 g of a filler (b2), to which are added 1.5 g of polyethyl silicate (crosslinking agent) per 100 g of slurry and x grams (y mmol) of the catalyst to be tested (d1).

For the zinc catalysts (according to the invention or for the comparative), the amounts tested are added to 1.5 ml of the solvent methyl tert-butyl ether (MTBE).

TABLE 1

Constituents of the RTV-2 compositions tested (polyethyl silicate crosslinking agent)

| Ingredients | Examples according to the invention (grams) | Comparative (UL28) (grams) |
|---|---|---|
| (a1) | 20.4 | 20.4 |
| (b1) | 61.3 | 61.3 |
| (b2) | 18.3 | 18.3 |
| (e) | 1.5 g per 100 g | 1.5 |
| (d1) | 2.66 mmol per 100 g of slurry | 0.886 mmol per 100 g of composition (0.44 g) |

In RTV-2, the tests are performed directly on a mixture consisting of ingredients (a1), (b1), (b2) and (e), to which is added and mixed the catalyst to be tested (d1). The working time or pot life is first measured (time after which the viscosity of the mixture prevents its use, i.e. the time required for the formation of a gel), and, from another mixture, a slug 6 mm thick is then cast and, after curing, the Shore A hardnesses (above and below) of a demolded slug 6 mm thick are measured under regulated conditions (23° C. and 50% relative humidity) and over increasing times. In the tables of results, the symbol ">" corresponds to the hardness values measured on the upper part of the slug and the symbol "<" corresponds to the hardness values measured on the lower part of the slug that is less exposed to the ambient air than the upper part. Measurement of the Shore A hardness, noted SAH=measurements performed according to the indications of standard ASTM-D 2240. The working time or pot life is the time beyond which the viscosity of the mixture prevents its use.

Two catalysts in comparative tests:
dimethyltin dineodecanoate (UL28) (test 1 bis), and
[Zn(ND)$_2$] with ND=neodecanoate=>[Zn(carboxylate)$_2$]

TABLE 2

RTV-2 tests - polyethyl silicate crosslinking agent and [Zn(neodecanoate)$_2$(amine)$_n$] complexes

| Tests | Catalyst tested (d1) | mg per 50 g of slurry | Working time (min) | Shore A hardness over 6 mm | | | |
|---|---|---|---|---|---|---|---|
| | | | | 1 day | | 4 days | |
| | | | | > | < | > | < |
| 1 | [Zn(ND)$_2$)] | 544 | >2 days | — | — | — | — |
| 1bis | UL28 | 220 | 40 | 24 | 23 | 26 | 26 |
| 2 | [Zn(ND)$_2$(OA)] | 716 | 157 | 10 | 6 | 20 | 17 |
| 3 | [Zn(ND)$_2$(OA)$_{1.5}$]* | 802 | 73 | 17 | 14 | 19 | 18 |
| 4 | [Zn(ND)$_2$(OA)$_2$] | 888 | 32 | 17 | 15 | 18 | 17 |
| 5 | [Zn(ND)$_2$(DBA)] | 716 | 120 | 10 | 7 | 19 | 16 |
| 6 | [Zn(ND)$_2$(DBA)$_{1.5}$]* | 802 | 53 | 16 | 13 | 20 | 18 |
| 7 | [Zn(ND)$_2$(DBA)$_2$] | 888 | 39 | 17 | 13 | 20 | 18 |

*In the case where 1.5 equivalents of amine are used relative to the zinc for the preparation of the catalyst, a mixture of complexes is obtained comprising 1 amine ligand or 2 amine ligands (which may also be in an oligomeric form) and, in this case, the nomenclature used to describe the complex is as follows: [Zn(carboxylate)$_2$(amine)$_{1.5}$].

For test 1 (comparative catalyst [Zn(ND)$_2$]), the slug was not hard enough to measure an SAH hardness after 1, 4 or 7 days (hence the symbol "-" in Table 2).

TABLE 3

RTV-2 tests - polyethyl silicate crosslinking agent and [Zn(naphthenate)$_2$(amine)$_n$] complexes

| Tests | Catalyst tested (d1) | mg per 50 g of slurry | Working time | Shore A hardness over 6 mm | | | |
|---|---|---|---|---|---|---|---|
| | | | | 1 day | | 4 days | |
| | | | | > | < | > | < |
| 8 | [Zn(NAPH)$_2$] | 714 | 48 h | — | — | — | — |
| 9 | [Zn(NAPH)$_2$(OA)] | 886 | 3 h 06 | 7 | 6 | 17 | 16 |
| 10 | [Zn(NAPH)$_2$(OA)$_2$] | 1058 | 30 min | 16 | 16 | 17 | 16 |
| 11 | [Zn(NAPH)$_2$(DBA)] | 886 | 2 h 48 min | 8 | 6 | 18 | 16 |
| 12 | [Zn(NAPH)$_2$(DBA)$_2$] | 1058 | 46 min | 17 | 15 | 19 | 18 |
| 13 | [Zn(NAPH)$_2$(DMBA)] | 849 | 7 h 15 min | <1 | <1 | 6c | 6 |
| 14 | [Zn(NAPH)$_2$(DMBA)$_2$] | 983 | 5 h 25 min | <1 | <1 | 14c | 15 |

For test 8 (comparative catalyst [Zn(NAPH)$_2$]), the slug was not hard enough to measure an SAH hardness after 1, 4 or 7 days (hence the symbol "-" in Table 3).

TABLE 4

RTV-2 tests - polyethyl silicate crosslinking agent and [Zn(2-ethylhexanoatenaphthenate)$_2$(amine)$_n$] complexes

| Tests | Catalyst tested (d1) | mg per 50 g of slurry | Working time | Shore A hardness over 6 mm | | | |
|---|---|---|---|---|---|---|---|
| | | | | 1 day | | 4 days | |
| | | | | > | < | > | < |
| 15 | [Zn(2-ethylhexanoate)$_2$] | 468 | 48 h | — | — | — | — |
| 16 | [Zn(2-ethylhexanoate)$_2$(DBA)] | 639 | 80 min | 13 | 12 | 24 | 21 |
| 17 | [Zn(2-ethylhexanoate)$_2$(DBA)$_2$] | 811 | 40 min | 17 | 14 | 16 | 19 |

For test 15 (comparative catalyst [Zn(2-ethylhexanoate)$_2$]), the slug was not hard enough to measure an SAH hardness after 1 or 4 days (hence the symbol "-" in Table 4).

Example 3

RTV-2 Two-Pack Composition—Crosslinking at 110° C.—Prepolymerized Vinyltrimethoxysilane or Ethyl Silicate Crosslinking Agent Part P2-1: the following mixture is prepared:
60 parts by weight of a slurry consisting of a mixture of α,ω-dihydroxylated polydimethylsiloxane oil (25.6% by weight, of viscosity 14 000 mPa·s) and Aerosil® 200 fumed silica treated in situ with hexamethyldisilazane (HMDZ) and with a specific surface area of 200 m$^2$/g,
20 parts by weight of an α,ω-dihydroxylated polydimethylsiloxane oil (viscosity 14 000 mPa·s),
18 parts by weight of ground quartz (sold by the company Sifraco), 1 part by weight of an α,ω-bis(dimethylhydroxysilyl) polydimethylsiloxane oil (dynamic viscosity at 25° C. of 750 mPa·s)

0.1 part of water, and 0.9 part by weight of a coloring base

Part P2-2: the following mixture is prepared:

73.8 parts by weight of a mixture of an α,ω-bis(dimethylhydroxysilyl)polydimethylsiloxane oil with a viscosity of 50 000 mPa·s, 5.8 parts by weight of an α,ω-bis(dimethylhydroxysilyl) polydimethylsiloxane oil with a dynamic viscosity at 25° C. of 14 000 mPa·s 11.5 parts by weight of silica A200 fumed silica Aerosil® 200 treated in situ by adding hexamethyldisilazane (HMDZ) and with a specific surface area of 200 m$^2$/g, and 8.9 parts of polydimethylsiloxane with a dynamic viscosity at 25° C. of 500 mPa·s.

For the parts P1: a crosslinking agent and the catalyst tested. Two types of crosslinking agents were used: a prepolymerized ethyl silicate (containing 14 mmol/g of ethoxy groups) and a prepolymerized vinyltrimethoxysilane (VTMO) (containing 14.2 mmol/g of methoxy).

Tests a) To a mixture of 49.25 g of part P2-1 and 0.75 g of crosslinking agent (advanced silicate) was added the catalyst to be tested:

716 mg of [Zn(ND)$_2$(OA)] (test 18), 802 mg of [Zn(ND)$_2$(OA)$_{1.5}$]* (test 19), 888 mg of [Zn(ND)$_2$(OA)$_2$]* (test 20).

Next, a small amount was deposited in a Teflon crucible and smoothed out to obtain a film with a thickness of between 0.5 and 1 mm, and the crucibles were placed in an oven at 110° C., at the hygrometry of the laboratory (about 35-40% at 25° C.).

Table 5 below gives the working time of the mixture (time after which the mixture no longer runs) and the crosslinking times in the oven at 110° C.

TABLE 5

RTV-2 composition - crosslinking at 110° C. - prepolymerized ethyl silicate crosslinking agent

| Tests | Catalyst | Working time at 25° C. | Crosslinking at 110° C. |
|---|---|---|---|
| 18 | [Zn(ND)$_2$(OA)] | 70 min | Crosslinked at 15 min and tacky feel at 30 min |
| 19 | [Zn(ND)$_2$(OA)$_{1.5}$]* | 35 min | Crosslinked at 8 min and non-tacky feel at 15 min |
| 20 | [Zn(ND)$_2$(OA)$_2$] | 17 min | Crosslinked at 7 min and non-tacky feel at 7 min |

*In the case where 1.5 equivalents of amine (octylamine) are used for the preparation of the catalyst, a mixture of complexes is obtained comprising 1 amine ligand or 2 amine ligands (which may also be in an oligomeric form) and, in this case, the nomenclature used to describe the complex is as follows: [Zn(carboxylate)$_2$(amine)$_{1.5}$].

For an RTV-2 two-pack application, requiring a rapid crosslinking rate with a non-tacky feel of the elastomer obtained after crosslinking, the catalyst according to the invention containing two amine ligands is more efficient than the one containing only one amine ligand.

b) To a mixture of 25 g of part P2-1 and 0.38 g of crosslinking agent (prepolymerized vinyltrimethoxysilane or VTMO containing 14.2 mmol/g of methoxy) was added the catalyst to be tested (444 mg in each of the tests).

A small amount was deposited in a Teflon crucible and smoothed out to obtain a film with a thickness of between 0.5 and 1 mm, and the crucibles were placed in an oven at 110° C., at the hygrometry of the laboratory (about 35-40% at 25° C.).

Table 6 below gives the working time of the mixture (time after which the mixture no longer runs) and the crosslinking times in the oven at 110° C.

TABLE 6

RTV-2 composition - crosslinking at 110° C. - VTMO crosslinking agent

| Tests | Catalyst | Working time at 25° C. | Crosslinking at 110° C. |
|---|---|---|---|
| 21 | [Zn(ND)$_2$(OA)$_2$] | 24 min | Crosslinked at 8 min and non-tacky feel at 8 min |
| 22 | [Zn(ND)$_2$(DBA)$_2$] | 35 min | Crosslinked at 10 min and tacky feel persists |

For an RTV-2 two-pack application, requiring a rapid crosslinking rate with a non-tacky feel of the elastomer obtained after crosslinking, the catalyst according to the invention containing two primary amine ligands (OA=n-octylamine) is more efficient than the one containing two secondary amine ligands (DBA=N,N-dibutylamine).

c) The activity of the complexes [Zn(ND)$_2$(OA)$_2$] and [Zn(ND)$_2$(DBA)$_2$] is evaluated with the base part P2-2 described above. To a mixture of 25 g of part P2-2 and either 0.715 g of precondensed ethyl silicate or 0.70 g of precondensed VTMO were added the catalysts (0.665 mmol). A small amount was deposited in a Teflon crucible and smoothed out to obtain a film with a thickness of between 0.5 and 1 mm, and the crucibles were placed in an oven at 110° C., at the hygrometry of the laboratory (about 35-40% at 25° C.).

TABLE 7

RTV-2 composition - crosslinking at 110° C.

| Tests | Catalyst | Working time | Crosslinking at 110° C. |
|---|---|---|---|
| | Precondensed silicate crosslinking agent | | |
| 23 | [Zn(ND)$_2$(OA)$_2$] | 10 min | Crosslinked at 5 min, transparent and non-tacky feel |
| 24 | [Zn(ND)$_2$(DBA)$_2$] | 13 min | Crosslinked at 8 min, transparent and tacky feel still at 8 min |
| | Precondensed VTMO crosslinking agent | | |
| 25 | [Zn(ND)$_2$(OA)$_2$] | 15 min | Crosslinked and non-tacky feel at 5 min |
| 26 | [Zn(ND)$_2$(DBA)$_2$] | <10 min | Crosslinked at 5 min but remains tacky |

For an RTV-2 two-pack application, requiring a rapid crosslinking rate with a non-tacky feel of the elastomer obtained after crosslinking, the catalyst according to the invention containing two primary amine ligands (OA=n-octylamine) is more efficient than the one containing two secondary amine ligands (DBA=N,N-dibutylamine).

c) The activity of the complexes [Zn(neodecanoate)$_2$(3-aminopropyltrimethoxysilane)$_2$] and [Zn(neodecanoate)$_2$(3-aminopropylmethyldiethoxysilane)$_2$] is evaluated with the base part P2-2 described above. To a mixture of 25 g of part P2-2 and either 0.715 g of precondensed ethyl silicate or 0.70 g of precondensed VTMO were added the catalysts (0.665 mmol). A small amount was deposited in a Teflon crucible and smoothed out to obtain a film with a thickness of between 0.5 and 1 mm, and the crucibles were placed in an oven at 110° C., at the hygrometry of the laboratory (about 35-40% at 25° C.).

TABLE 8

RTV-2 composition - crosslinking at 110° C.

| Tests | | Working time | Crosslinking at 110° C. |
|---|---|---|---|
| | Precondensed silicate crosslinking agent | | |
| 27 | [Zn(neodecanoate)$_2$(3-aminopropylmethyldiethoxysilane)$_2$] | 30 min | Crosslinked at 7 min, transparent and non-tacky feel |
| | Precondensed VTMO crosslinking agent | | |
| 28 | [Zn(neodecanoate)$_2$(3-aminopropyltrimethoxysilane)$_2$] | 20 min | Crosslinked at 5 min, transparent and non-tacky feel |

For applications as a hot thin coat requiring adhesion, the aminosilane-zinc carboxylate complexes show excellent activity with crosslinking agents of both methoxy and ethoxy type.

Examples 4 to 8

RTV-2 Two-Pack Composition for Molding Application (Organosilicon Compounds A=α,ω-Dihydroxylated Polydimethylsiloxane; Alkoxy Crosslinking Agent)

In the Present Examples:
the "pot life" corresponds to a gelation time at 23° C., in minutes, measured with an automatic machine with alternating movement according to AFNOR standard NF T-77 107,
the abbreviation "SAH" means the Shore A (written ShA) hardness, measured on the confined face of a slug 6 mm thick according to standard ASTM D-2240. The SAH indicated in parentheses corresponds to the hardness measured on the upper face of the slug (in contact with the air),
the "SAH 24 h" corresponds to the hardness after 24 hours of crosslinking at room temperature,
the "final SAH" corresponds to the hardness after total crosslinking at room temperature,
the abbreviation "BS" means the breaking strength, in MPa, according to AFNOR standard NF T-46002,
the abbreviation "EB" means the elongation at break, in %, according to preceding standard,
the abbreviation "Ts" means the test strength in N/mm.

A two-pack composition comprising parts P1 and P2 is prepared, the compositions of which are described in Table 9.

1) Nature of the Ingredients Mentioned in Part P2 of the Compositions Tested a: Slurry consisting of a mixture of α,ω-bis(dimethylhydroxysilyl)polydimethylsiloxane oil (25.6% by weight, of viscosity 14 000 mPa·s) and Aerosil® 200 fumed silica treated in situ with hexamethyldisilazane (HMDZ) and with a specific surface area of 200 m²/g,
b1: Polydimethylsiloxane oil blocked at each of the chain ends with an (HO)(CH$_3$)$_2$SiO$_{1/2}$ unit, having a dynamic viscosity of 14 000 mPa·s at 25° C.
b2: Polydimethylsiloxane oil blocked at each of the chain ends with an (HO)(CH$_3$)$_2$SiO$_{1/2}$ unit, having a dynamic viscosity of 3500 mPa·s at 25° C.
c: Ground quartz (sold by the company Sifraco),
d: Polydimethylsiloxane oil blocked at each of the chain ends with an (HO)(CH$_3$)$_2$SiO$_{1/2}$ unit, having a dynamic viscosity of 750 mPa·s at 25° C.
e: Water
f: Coloring base 2) Nature of the Ingredients Mentioned in Part P1 of the Compositions g1,x: Catalyst Zn(ND)$_2$(OA)$_x$
g2,x: Catalyst Zn(ND)$_2$(DBA)$_x$
g3: Dimethyltin dineodecanoate, of formula [C$_9$H$_{19}$COO]$_2$Sn(Me)$_2$], sold under the reference Fomrez® Catalyst UL-28
h1: Partially hydrolyzed and condensed ethyl silicate, characterized by a content of (OEt) unit=14 mmol/g
h2: Propyl silicate, characterized by a content of (OPr) units=13.3 mmol/g
h3: Trimethoxyphenylsilane
i: Polydimethylsiloxane oil blocked at each of the chain ends with a (CH$_3$)$_3$SiO$_{1/2}$ unit, having a viscosity of 50 mPa·s at 25° C.
j: Plasticizer sold under the name Mediaplast.
Tables 9 and 10 below describe the compositions tested:

TABLE 9

Components of the parts P2

| Part P2 | P2-a | P2-b | P2-c |
|---|---|---|---|
| a1 | 60.2 | 60.2 | 60.2 |
| b1 | 20 | 0 | 0 |
| b2 | 0 | 20 | 20 |
| c | 18 | 18 | 18 |
| d | 1 | 1 | 1 |
| e | 0.1 | 0.1 | 0 |
| f | 0.7 | 0.7 | 0.8 |

TABLE 10

Components of the parts P1

Part P1

| | P1-a | P1-b | P1-c | P1-d | P1-e | P1-f | P1-g | P1-i | P1-j | P1-k | P1-l | P1-h Comparative |
|---|---|---|---|---|---|---|---|---|---|---|---|---|
| x | x = 1 | x = 1.2* | x = 1.4* | x = 1.5* | x = 2 | x = 1.5* | x = 2 | x = 1.5* | x = 1.5* | x = 1.5* | x = 1.5* | x = 1.5* |
| g1,x | 17.5 | 18.5 | 19.4 | 19.9 | 23.9 | | | 19.9 | 19.9 | | | |
| | (2 eq) | (2 eq) | (2 eq) | (2 eq) | (2 eq) | | | (2 eq) | (2 eq) | | | |

TABLE 10-continued

Components of the parts P1

Part P1

|  | P1-a | P1-b | P1-c | P1-d | P1-e | P1-f | P1-g | P1-i | P1-j | P1-k | P1-l | P1-h Comparative |
|---|---|---|---|---|---|---|---|---|---|---|---|---|
| g2,x |  |  |  |  |  | 21.6 (2 eq) | 23.9 (2 eq) |  |  | 21.6 (2 eq) | 21.6 (2 eq) |  |
| g3 |  |  |  |  |  |  |  |  |  |  |  | 8.8 (1 eq) |
| h1 | 30 | 30 | 30 | 30 | 30 | 30 | 30 | 40 | 50 | 40 | 50 | 30 |
| i + j | 52.5 | 51.5 | 50.6 | 50.3 | 46.1 | 48.4 | 46.1 | 40.1 | 30.1 | 38.4 | 28.4 | 61.2 |

*In the case where between 1 and 2 equivalents of amine are used, i.e. 1.2, 1.4 or 1.5 equivalents of amine for the preparation of the catalyst according to the invention, a mixture of complexes is obtained comprising 1 amine ligand and 2 amine ligands (which may also be in an oligomeric form).

3) Implementation

To 100 parts by weight of component or part P2 are added 5 parts by weight of component P1. Crosslinking is obtained after manual mixing using a spatula, at 23° C. The crosslinking kinetics profile is expressed by the pot life and the SAH 24 h measurement. The properties of the crosslinked elastomer are measured (final SAH and optionally the mechanical properties).

4) Tests

4a) Examples 4

In these examples, RTV-2 products are prepared by mixing the part P2-b with parts P1 containing a catalyst of mean formula [Zn(ND)$_2$(Amine)$_{1.5}$]* (with Amine=OA or DBA) and various amounts of partially hydrolyzed and condensed ethyl silicate as crosslinking agent. The compositions are detailed in tables 9 and 10. The results are given in Table 11 below.

The above examples demonstrate the efficacy of these novel catalysts:

- to catalyze the polycondensation reaction with an advantageous kinetics profile for the molding application. Specifically, when an OR/OH mole ratio of between 13 and 21 and preferably between 15 and 19 is used, a good compromise is achieved in terms of pot life (working time) without loss of a hardness at 24 hours and finally. Furthermore, it is noted that the crosslinking takes place in the same manner when confined and on contact with air (specifically, the SAH results are equivalent on the confined face and on the upper face).
- to form an elastomeric network with good mechanical properties, similar to those conventionally obtained with tin.

4b) Examples 5 and 6

In these examples, catalysts with a mean formula [Zn(ND)$_2$(OA)$_x$] or [Zn(ND)$_2$(DBA)$_x$] are prepared by varying the value of the number of equivalents of amine during the synthesis of the catalyst (desired stoichiometry of between 1 and 2 molar equivalents of amine relative to the zinc). RTV-2 products are then prepared by mixing a part P2 (a or b) with parts P1 containing the synthesized catalyst of mean formula [Zn(ND)$_2$(Amine)$_x$]* (with Amine=OA or DBA) and a given amount of partially hydrolyzed and condensed ethyl silicate as crosslinking agent. The compositions are detailed in tables 9 and 10. The results are given in Table 12 below.

TABLE 11

Examples according to the invention and comparative example

|  | Examples | | | | | | |
|---|---|---|---|---|---|---|---|
|  | 4a | 4b | 4c | 4d | 4e | 4f | Comp 4g |
| Part P2 | P2-b | P2-b | P2-b | P2-b | P2-b | P2-b | P2-b |
| Part P1 | P1-d | P1-i | P1-j | P1-f | P1-k | P1-l | Comp. P1h |
| Catalyst | [Zn(ND)$_2$(OA)$_{1.5}$]* | | | [Zn(ND)$_2$(DBA)$_{1.5}$]* | | | UL28 |
| OR/OH | 13 | 17 | 21 | 13 | 17 | 21 | 13 |
| Evaluation | | | | | | | |
| Pot life | 87 | 89 | 92 | 118 | 103 | 88 | 91 |
| SAH 24 h | 14 (15) | 18 (20) | 18 (21) | 11 (11) | 14 (16) | 17 (19) | 22 (23) |
| Final SAH | 23 (24) | 25 (26) | 27 (29) | 20 (22) | 24 (25) | 28 (29) | 27 (27) |
| BS | / | 3.5 | / | / | / | 4 | 3.8 |
| EB | / | 360 | / | / | / | 320 | 325 |
| Ts | / | 22 | / | / | / | 21 | 21 |

*The ratio OR/OH = mole ratio (alcoxy function (OR) of the crosslinking agent)/(OH function of polyorganosiloxane silanol type α,ω-bis(dimethylhydroxysilyl)polydimethylsiloxane).

TABLE 12

Examples according to the invention

| | [Zn(ND)$_2$(OA)$_x$] Examples | | | | | [Zn(ND)$_2$(OA)$_x$] | |
|---|---|---|---|---|---|---|---|
| | 5a | 5b | 5c | 5d | 5e | 5f | 5g |
| Part P2 | P2-a (based on b1 - Viscosity = 14 000 mPa · s); OR/OH = 14 | | | | | | |
| Part P1 | P1-a | P1-b | P1-c | P1-d | P1-e | P1-f | P1-g |
| Pot life | 106 | 83 | 55 | 37 | 30 | 57 | 31 |
| SAH 24 h | 6 (7) | 10 (10) | 13 (14) | 13 (14) | 15 (16) | 9 (9) | 13 (15) |
| Final SAH | 21 (23) | 21 (23) | 22 (23) | 21 (23) | 20 (22) | 20 (22) | 20 (22) |

| | Examples | | | | | | |
|---|---|---|---|---|---|---|---|
| | 6a | 6b | 6c | 4a | 6d | 4d | 6e |
| Part P2 | P2-b (based on b2 - Viscosity = 3500 mPa · s); OR/OH = 13 | | | | | | |
| Part P1 | P1-a | P1-b | P1-c | P1-d | P1-e | P1-f | P1-g |
| Pot life | 244 | 173 | 119 | 87 | 72 | 118 | 77 |
| SAH 24 h | 5 (6) | 7 (8) | 12 (14) | 14 (15) | 15 (17) | 11 (11) | 14 (15) |
| Final SAH | 22 (24) | 24 (24) | 22 (24) | 23 (24) | 19 (21) | 20 (22) | 22 (24) |

The above examples show that the reactivity of the amino zinc dicarboxylate catalyst according to the invention may be modified by adjusting the number of amine ligands: specifically, when the zinc dicarboxylate catalyst is richer in amine ligand (two ligands versus one ligand), the reactivity increases and the pot life decreases. The final hardness is constant. Furthermore, it is noted that it is possible to increase the pot life (=lifetime of the bath) by replacing only the α,ω-di(dimethylhydroxysilyl)polydimethylsiloxane) oil with a dynamic viscosity at 25° C. of 14 000 mPa·s used in the part P2-a with an α,ω-di(dimethylhydroxysilyl)polydimethylsiloxane) oil of lower viscosity 3500 mPa·s (part P2-b), without deteriorating the SAH 24 h hardness or the final SAH hardness.

4c) Example 7

In this example, RTV-2 products are prepared by mixing parts P2 containing or not containing water (P2-b or P2-c) with a part P1 containing a catalyst of mean formula Zn(ND)$_2$(OA)$_{1.5}$ and a given amount of partially hydrolyzed and condensed ethyl silicate as crosslinking agent. The compositions are detailed in tables 9 and 10. The results are given in Table 13 below.

TABLE 13

Examples according to the invention
with the catalyst [Zn(ND)$_2$(OA)$_{1.5}$]*

| Examples | 7a | 4b |
|---|---|---|
| Part P2 | P2-c (0% water) | P2-b (0.1% water) |
| Part P1 | P1-i | P1-i |
| Pot life | 96 | 89 |
| SAH 24 h | 18 (20) | 18 (20) |
| Final SAH | 24 (26) | 25 (26) |

The above examples show that the zinc dicarboxylate catalysts do not require the addition of water to the medium in order to be active, in contrast with the standard tin-based catalysts, which, when formulated in two-pack form (RTV-2), require the presence of water in one of the parts of the two-pack product to improve the reactivity.

4d) Example 8

In this example, RTV-2 products are prepared by mixing a part P2-b with parts P1 containing a catalyst of mean formula [Zn(ND)$_2$(OA)$_{1.5}$]* and various crosslinking agents. The compositions are detailed in Tables 9 (Part P2-b) and 14 (Part P1). The results are given in Table 15 below.

TABLE 14

| Part P1 | P1-f | P1-m | P1-n |
|---|---|---|---|
| x | x = 1.5 | x = 1.5 | x = 1.5 |
| g2, x | 21.6 (2eq) | 24.7 (2eq) | 24.7 (2eq) |
| h1 | 30 | 22 | 22 |
| h2 | | 8 | |
| h3 | | | 8 |
| i + j | 48.4 | 45.3 | 45.3 |

TABLE 15

| Examples | 4d | 8a | 8b |
|---|---|---|---|
| Part P2 | P2-b | P2-b | P2-b |
| Part P1 | P1-f | P1-m | P1-n |
| Pot life | 118 | 139 | 88 |
| SAH 24 h | 11 (11) | 8 (8) | 8 (8) |
| Final SAH | 20 (22) | 20 (21) | 18 (20) |

The above examples show the efficacy of the novel catalysts for forming networks with different alkoxylated crosslinking agents and varied kinetic profiles.

Example 9

Formulation of an RTV-2 Two-Pack Product (Alkoxy Crosslinking Agent) for Coating on Lace Consisting of a Polyamide+Elastane Fabric Two types of formulation were tested under several crosslinking conditions: temperature, humidity, addition of water, dose of catalyst.

Abbreviations used in this example:
ND=neodecanoate
OA=octylamine
AMEO=aminopropyltriethoxysilane
HMDZ=hexamethyldisilazane
DS6490: Dynasylan® 6490 partially hydrolysed and condensed vinyltrimethoxysilane (VTMO)=>Partially hydrolyzed and condensed ethyl silicate, characterized by a content of (OEt) unit=14 mmol/g The mixtures are prepared in a Speed-Mixer, by introducing, in the following order, the slurry (part P2) and then part P1 (crosslinking agent+catalyst). The following composition is obtained:
25 g of slurry TCS 7370
0.715 g of crosslinking agent (DS6490) or
x mmol of catalyst ([Zn(ND)$_2$(AMEO)$_2$] or [Zn(ND)$_2$(OA)$_2$])

The coatings are performed using a 0.5 mm doctor blade on a lace consisting of a polyamide+elastane fabric (coating thickness=0.41-0.48 mm). The crosslinking is performed at 80° C. in a ventilated oven. The blocking force makes it possible to check that the coating is crosslinked on exiting the oven: a value of between 2 and 4.5 N/2 cm is desired for a good result. It is measured by folding the coated lace on itself as it leaves the oven (with a coated contact face on a coated face) and then by placing a weight of about 1 kg on the specimen for 24 hours, followed by performing a peel test to check whether the silicone coating does or does not bond to itself. The results are given in Table 16 below.

TABLE 16

| Test | Catalyst | Content of catalyst (mmol) | Time (min) | Blocking (N/2 cm) |
|---|---|---|---|---|
| 9-1 | [Zn(ND)$_2$(AMEO)$_2$] | 0.665 | 10 | 4.40 |

The same experiment is performed, but replacing the crosslinking agent (DS6490) with a partially hydrolysed and condensed ethyl silicate (same number of molar equivalents) and doubling the number of equivalents of catalyst tested (1.33 mmol instead of 0.665 mmol in the preceding test). The results are given in Table 17 below.

TABLE 17

| Test | Catalyst | Content of catalyst (mmol) | Time (mn) | Blocking (N/2 cm) |
|---|---|---|---|---|
| 9-2 | [Zn(ND)$_2$(OA)$_2$] | 1.33 | 10 | 2.02 |
| 9-3 | [Zn(ND)$_2$(AMEO)$_2$] | 1.33 | 10 | 1.91 |

Good results are obtained for the blocking property.

Example 10

Comparative Example

Comparative Example 4 of patent application US 2008/0207 938 was repeated:
Composition 10-1:
750 g of an α,ω-bis(dimethylhydroxysilyl)polydimethylsiloxane oil with a dynamic viscosity at 25° C. of 75 000 mPa·s
135 g of an α,ω-bis(trimethylsilyl)polydimethylsiloxane oil with a dynamic viscosity at 25° C. of 1000 mPa·s
10.3 g of methyltrimethoxysilane
5.0 g of vinyltrimethoxysilane
0.16 g of zinc octoate (0.45 mmol)
0.32 g of dibutylamine (2.48 mmol)

Composition 10-1 is mixed for 10 minutes protected from the moisture of the ambient air. After 72 hours, silanol groups are still detected by the protocol described in this example, indicating that the silanol groups have not reacted. Thus, this prior art example shows that a mixture of zinc octoate and of dibutylamine (in molar excess) does not allow functionalization (protection of the silanol groups as alkoxylated groups that are stable on storage).

Example 11

Abbreviation: ND: neodecanoate
70 g of an α,ω-bis(dimethylhydroxysilyl)polydimethylsiloxane oil with a dynamic viscosity at 25° C. of 750 mPa·s (48V750 oil), 6 g of methyltriethoxysilane (MTMS) and 3 g of vinyltrimethoxysilane (VTMO) are mixed in a 100 ml polypropylene jar, the catalyst to be tested is added and the mixture is stirred at 700 rpm with a magnetic bar and under an argon atmosphere, i.e. in the absence of atmospheric moisture, for 1 hour to perform the functionalization. The mixture is then poured into the lid of the container and placed in contact with atmospheric moisture so as to estimate the catalytic effect on the curing of the composition. The activity of the catalyst [Zn(ND)$_2$(DBA)] was compared with the separate addition of the complex [Zn(ND)$_2$] followed by the addition of an amount of two molar equivalents of N,N-dibutylamine (DBA) to evaluate whether the catalyst tested can cure a silicone composition that is curable on contact with atmospheric moisture.

TABLE 18

| Catalysts | Appearance of the composition after 24 hours in contact with atmospheric moisture |
|---|---|
| Invention: [Zn(ND)$_2$(DBA)] 190 mg (0.35 mmol) | Elastomer crosslinked deep down |
| Invention: [Zn(ND)2(DBA)2] 235 mg (0.35 mmol) | Elastomer crosslinked deep down |
| Comparative example: [Zn(ND)$_2$] (143 mg) then 2 eq. DBA (92 mg = 128 μl) | Non-crosslinked viscous composition |

Verification of the Efficacy of the Catalysts According to the Invention as Functionalization Catalyst (Protection of the Silanol Groups as Alkoxylated Groups that are Stable on Storage)

70 g of an α,ω-bis(dimethylhydroxysilyl)polydimethylsiloxane oil with a dynamic viscosity at 25° C. of 750 mPa·s (48V750 oil), 6 g of methyltriethoxysilane (MTMS) and 3 g of vinyltrimethoxysilane (VTMO) are mixed in a 100 ml polypropylene jar, stirring with a magnetic bar and under an argon atmosphere. The catalyst is added (with stirring between each addition) and the mixture is stirred at 700 rpm. Samples (about 0.5 ml) are taken after 15 min, 13 min, 1 hour or more. A few drops of butyl titanate are added to the samples taken. If the conversion is not complete, a gel forms instantaneously during mixing with a spatula. If the conversion is complete, the mixture remains fluid.

The results are given in the table below:

TABLE 19

| Catalyst according to the invention added | Functionalization complete in |
|---|---|
| [Zn(ND)$_2$(DBA)] 190 mg (0.35 mmol) | 1 h |
| [Zn(ND)$_2$(DBA)$_2$] 235 mg (0.35 mmol) | 1 h |

The invention claimed is:
1. A composition comprising:
at least one organosilicon compound A comprising at least two identical or different hydrolyzable and condensable groups, or at least two silanol functions =SiOH,
at least one crosslinking agent B,
optionally at least one filler C, and a catalytically effective amount of at least one polycondensation catalyst M which is a zinc complex comprising in its structure two types of ligand: carboxylate and amine, in which the polycondensation catalyst(s) M is obtained:

a) by reacting per 1 mol of at least one zinc dicarboxylate of formula [Zn(carboxylate)$_2$] or of a mixture of two different zinc dicarboxylates mol of amine or a mixture of amines optionally in the presence of a solvent, so as to obtain a reaction product comprising:

x mol of a zinc complex A which is a [(Zn(carboxylate)$_2$(amine)] complex, y mol of a zinc complex B which is a [(Zn(carboxylate)$_2$(amine)$_2$] complex, with x≥0, y≥0, optionally X$^3$ mol of unreacted zinc dicarboxylate, and optionally X$^4$ mol of residual unreacted amine, and b) after optionally removing the solvent and the residual amine, the polycondensation catalyst(s) M are recovered in the form of at least one zinc complex A, at least one zinc complex B or a mixture of zinc complex A and of zinc complex B, with optionally a residual amount of X$^3$ mol of the complex [Zn(carboxylate)$_2$], and the symbols X$^1$, X$^3$ and X$^4$ are numbers and the sum x+y+X$^3$=1.

2. A composition, comprising:

at least one organosilicon compound A comprising at least two identical or different hydrolyzable and condensable groups, or at least two silanol functions ≡SiOH, at least one crosslinking agent B, optionally at least one filler C, and a catalytically effective amount of at least one polycondensation catalyst M which is a complex of formula (1) below:

$$[Zn(C^1)_{n'}(C^2)_{n''}(L^1)_{y'}(X)_{z'}]_{z'} \cdot (H_2O)_{x''} \qquad (1)$$

in which:

the symbols C$^1$ and C$^2$ are identical or different ligands chosen from the group of carboxylates, the symbols n' and n" represent the number of carboxylate ligands and are integers equal to 0, 1 or 2 with the condition that the sum n'+n"=2, the symbols L$^1$ and L$^2$ are identical or different ligands chosen from the group of amines, the symbols y' and y" represent the number of amine ligands and are integers equal to 0, 1 or 2 with the condition that the sum y'+y"=1 or 2, the symbol X is a ligand other than C$^1$, C$^2$, L$^1$ and L$^2$, the symbol x'≥0, the symbol x"≥0, 4, and the symbol z' is an integer greater than or equal to 1.

3. The composition as claimed in claim 2, in which the polycondensation catalyst M is a complex of formula (2) below:

$$[Zn(C^1)_{n'}(C^2)_{n''}(L^1)_{y'}(L^2)_{y''}]_{z'} \qquad (2)$$

in which:

the symbols C$^1$ and C$^2$ are identical or different ligands chosen from the group of carboxylates, the symbols n' and n" represent the number of carboxylate ligands and are integers equal to 0, 1 or 2 with the condition that the sum n'+n"=2, the symbols L$^1$ and L$^2$ are identical or different ligands chosen from the group of amines, the symbols y' and y" represent the number of amine ligands and are integers equal to 0, 1 or 2 with the condition that the sum y'+y"=1 or 2, and the symbol z' is an integer greater than or equal to 1.

4. The composition as claimed in claim 2, in which the polycondensation catalyst M is a complex of formula (3) below:

$$[Zn(C^1)_2(L^1)_{y'}]_{z'} \qquad (3)$$

in which:

the symbol C$^1$ is a ligand chosen from the group of carboxylates, the symbol L$^1$ is a ligand chosen from the group of amines, the symbol y' is a number equal to 1 or 2, and the symbol z' is an integer greater than or equal to 1.

5. The composition as claimed in claim 2, in which the ligand of amine type L$^1$ or L$^2$ is chosen from the group consisting of primary monoamines of alkylamine type containing in total from 1 to 40 carbon atoms for the alkyl radical, secondary monoamines of dialkylamine type containing in total from 2 to 40 carbon atoms for the alkyl radicals, tertiary monoamines of trialkylamine type containing in total from 3 to 60 carbon atoms for the alkyl radicals, alkyl diamines containing in total from 1 to 40 carbon atoms for the alkyl radicals and amino silanes.

6. The composition as claimed in claim 2, in which the ligand of amine type L$^1$ or L$^2$ is chosen from the group consisting of the following amines: N,N-dimethylethylenediamine, N,N'-dimethylethylenediamine, N,N,N'-trimethylethylenediamine, N,N'-diisopropylethylenediamine, n-butylamine, n-propylamine, n-heptylamine, n-octylamine, n-nonylamime, tert-butylamine, isopropylamine, 2-ethylhexylamine, decylamine, dodecylamine, which may be linear or branched, N-methyl-N-butylamine, N,N-dipropylamine, N,N-diisopropylamine, N-ethyl-N-butylamine, N,N-dibutylamine, N,N-dimethyl-N-butylamine, di(n-octyl)amine, N-n-propylethylenediamine, N,N,N',N'-tetramethylethylenediamine, 3-aminopropyltrimethoxysilane and 3-aminopropylmethyldiethoxysilane.

7. The composition as claimed in claim 2, in which the ligand of carboxylate type C$^1$ or C$^2$ is chosen from the group consisting of the carboxylates of empirical formula [C$_{10}$H$_{19}$O$_2$]$^-$.

8. The composition as claimed in claim 2, in which the polycondensation catalyst M is a complex of formula (3") below:

$$[Zn(C^1)_2(L^1)_{y'}]_{z'} \qquad (3')$$

in which:

the symbol C$^1$ is a neodecanoate or naphthenate ligand or a 2-ethylhexanoate ligand, the symbol L$^1$ is a ligand chosen from the group consisting of the following compounds: N,N-dimethylethylenediamine, N,N'-dimethylethylenediamine, N,N,N'-trimethylethylenediamine, N,N'-diisopropylethylenediamine, n-butylamine, n-propylamine, n-heptylamine, n-octylamine, n-nonylamime, tert-butylamine, isopropylamine, 2-ethylhexylamine, decylamine, dodecylamine, which may be linear or branched, N-methyl-N-butylamine, N,N-dipropylamine, N,N-diisopropylamine, N-ethyl-N-butylamine, N,N-dibutylamine, N,N-dimethyl-N-butylamine, di(n-octyl)amine, N-n-propylethylenediamine, N,N'-dimethylethylenediamine, N,N,N',N'- tetramethylethylenediamine, 3-aminopropyltrimethoxysilane and 3-aminopropylmethyldiethoxysilane, the symbol y' is an integer equal to 1 or 2, and the symbol z'=1, 2, 3 or 4.

9. The composition as claimed in claim 2, in which the polycondensation catalyst M is a complex chosen from the group consisting of the following complexes:

[Zn(naphthenate)$_2$ (bis(2-ethylhexyl)amine)],
[Zn(naphthenate)$_2$ (bis(2-ethylhexyl)amine)$_2$],
[Zn(naphthenate)$_2$ (diisononylamine)],
[Zn(naphthenate)$_2$ (diisononylamine)$_2$],
[Zn(naphthenate)$_2$ (di(n-octyl)amine)],
[Zn(naphthenate)$_2$ (di(n-octyl)amine)$_2$],
[Zn(naphthenate)$_2$(n-octylamine)],
[Zn(naphthenate)$_2$(n-octylamine)$_2$],
[Zn(naphthenate)$_2$(N,N-dibutylamine)],
[Zn(naphthenate)$_2$(N,N-dibutylamine)$_2$],
[Zn(naphthenate)$_2$(N,N-dimethyl-N-butylamine)$_2$],
[Zn(naphthenate)$_2$(N,N-dimethyl-N-butylamine)$_2$],
[Zn(naphthenate)$_2$(aminoethylaminopropyltrimethoxysilane)],
[Zn(naphthenate)$_2$(aminoethylaminopropyltrimethoxysilane)$_2$],
[Zn(naphthenate)$_2$(aminopropyltriethoxysilane)],
[Zn(naphthenate)$_2$(aminopropyltriethoxysilane)$_2$],
[Zn(neodecanoate)$_2$(di(n-octyl)amine)],
[Zn(neodecanoate)$_2$(di(n-octyl)amine)$_2$],
[Zn(neodecanoate)$_2$(n-octylamine)],
[Zn(neodecanoate)$_2$(n-octylamine)$_2$],
[Zn(neodecanoate)$_2$(N,N-dibutylamine)],
[Zn(neodecanoate)$_2$(N,N-dibutylamine)$_2$],
[Zn(neodecanoate)$_2$(3-aminopropyltrimethoxysilane)$_2$],
[Zn(neodecanoate)$_2$ (3-aminopropylmethyldiethoxysilane)$_2$],
[Zn(neodecanoate)$_2$ (aminoethylaminopropyltrimethoxysilane)],
[Zn(neodecanoate)$_2$ (aminoethylaminopropyltrimethoxysilane)$_2$],
[Zn(neodecanoate)$_2$ (aminopropyltriethoxysilane)],
[Zn(neodecanoate)$_2$ (aminopropyltriethoxysilane)$_2$],
[Zn(neodecanoate)$_2$ (bis(2-ethylhexyl)amine)],
[Zn(neodecanoate)$_2$ (bis(2-ethylhexyl)amine)$_2$],
[Zn(neodecanoate)$_2$ (diisononylamine)],
[Zn(neodecanoate)$_2$ (diisononylamine)$_2$],
[Zn(2-ethylhexanoate)$_2$(N,N-dibutylamine)],
[Zn(2-ethylhexanoate)$_2$(N,N-dibutylamine)$_2$],
[Zn(2-ethylhexanoate)$_2$(n-octylamine)],
[Zn(2-ethylhexanoate)$_2$(n-octylamine)$_2$],
[Zn(2-ethylhexanoate)$_2$ (bis(2-ethylhexyl)amine)],
[Zn(2-ethylhexanoate)$_2$ (bis(2-ethylhexyl)amine)$_2$],
[Zn(2-ethylhexanoate)$_2$ (diisononylamine)],
[Zn(2-ethylhexanoate)$_2$ (diisononylamine)$_2$], and
mixtures thereof.

10. The composition as claimed in claim 2, in which the organosilicon compound A is a polyorganosiloxane comprising:

(i) at least two siloxyl units of formula (4) below:

 (4)

in which:

the symbols R$^1$, which may be identical or different, represent C$_1$ to C$_{30}$ monovalent hydrocarbon-based radicals, the symbols Z, which may be identical or different, each represent a hydrolyzable and condensable group or a hydroxyl group, a is equal to 0, 1 or 2, b is equal to 1, 2 or 3, the sum a+b is equal to 1, 2 or 3, and optionally (ii) one or more siloxyl units of formula (5) below:

 (5)

in which:

the symbols R, which may be identical or different, represent C$_1$ to C$_{30}$ monovalent hydrocarbon-based radicals optionally substituted with one or more halogen atoms or with amino, ether, ester, epoxy, mercapto or cyano groups, and the symbol c is equal to 0, 1, 2 or 3.

11. The composition as claimed in claim 2, in which the crosslinking agent B is a silicon compound, each molecule of which comprises at least three hydrolyzable and condensible groups Y and said crosslinking agent B having the formula (7) below:

 (7)

in which formula:

the symbol R' is a monovalent hydrocarbon-based radical comprising from 1 to 30 carbon atoms, the symbol Y is an alkoxy, alkoxy-alkylene-oxy, amino, amido, acylamino, aminoxy, iminoxy, ketiminoxy, acyloxy or enoxy group, the symbol a=3 or 4.

12. The composition as claimed in claim 2, not containing any catalyst containing in its structure at least one tin atom.

13. The composition as claimed in claim 2, in which the polycondensation catalyst M is the only polycondensation catalyst present in said composition, which may optionally contain at least one functionalization catalyst.

14. An RTV-1 one-pack composition which is in a single airtight package P, comprising a composition as claimed in claim 2.

15. An elastomer obtained by placing in contact with atmospheric moisture the contents of the package P of the RTV-1 one-pack composition according to claim 14 and leaving said contents to cure.

16. A process for coating the composition as defined according to claim 2 onto a flexible support S which is made of textile, paper, polyvinyl chloride, polyester, polypropylene, polyamide, polyethylene, polyurethane or polyethylene terephthalate, comprising the following a), b) and c):

a) the composition is prepared, b) said composition is then deposited in continuous or batch manner onto said flexible support S, and c) said silicone composition X is left to crosslink in the presence of moisture provided by the ambient air or by prior addition of water so as to form a silicone elastomer.

17. An elastomer obtained by leaving the composition of claim 2 to cure in the presence of water or of atmospheric moisture.

18. An RTV-2 two-pack composition, which is in two separate packages P1 and P2, wherein:

the package P1, which is airtight, comprises:

a catalytically effective amount of at least one polycondensation catalyst M, and at least one crosslinking agent, and the package P2 does not contain said polycondensation catalyst M and said crosslinking agent B and comprises:

per 100 parts by weight of at least one organosilicon compound A comprising at least two identical or different hydrolyzable and condensable groups, or at least two silanol functions ≡SiOH
and
from 0 to 10 part(s) by weight of water,
wherein catalyst M which is a complex of formula (1) below:

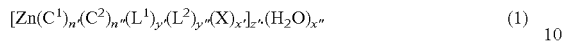 (1)

in which:
the symbols $C^1$ and $C^2$ are identical or different ligands chosen from the group of carboxylates,
the symbols n' and n" represent the number of carboxylate ligands and are integers equal to 0, 1 or 2 with the condition that the sum n'+n"=2,
the symbols $L^1$ and $L^2$ are identical or different ligands chosen from the group of amines,
the symbols y' and y" represent the number of amine ligands and are integers equal to 0, 1 or 2 with the condition that the sum y'+y"=1 or 2,
the symbol X is a ligand other than $C^1$, $C^2$, $L^1$ and $L^2$,
the symbol x'≥0,
the symbol x"≥0, an, and
the symbol z' is an integer greater than or equal to 1.

19. The composition as claimed in claim 18, in which the organosilicon compound A is a polyorganosiloxane comprising at least two silanol groups ≡SiOH and whose weight-average molar mass $M_w$ is greater than or equal to twice the entanglement molar mass $M_e$.

20. An RTV-2 two-pack composition as claimed in claim 18, which is for molding application, which is in two separate packages P1 and P2, wherein:
the package P1, which is airtight, comprises:
a catalytically effective amount of at least one polycondensation catalyst M, and
at least one crosslinking agent B,
and
the package P2 does not contain said polycondensation catalyst M and said crosslinking agent B and comprises:
per 100 parts by weight of at least one organosilicon compound A which is a α,ω-dihydroxylated polydimethylsiloxane whose viscosity is between 2000 mPa·s and 5000 mPa·s, and
from 0 to 10 part(s) by weight of water.

21. An elastomer obtained:
after mixing the contents of the packages P1 and P2 of the RTV-2 two-pack composition as defined according to claim 18 and leaving the mixture to cure.

22. A complex having the following formula:
[Zn(naphthenate)$_2$ (bis(2-ethylhexyl)amine)],
[Zn(naphthenate)$_2$ (bis(2-ethylhexyl)amine)$_2$],
[Zn(naphthenate)$_2$ (diisononylamine)],
[Zn(naphthenate)$_2$ (diisononylamine)$_2$],
[Zn(naphthenate)$_2$ (di(n-octyl)amine)],
[Zn(naphthenate)$_2$ (di(n-octyl)amine)$_2$],
[Zn(naphthenate)$_2$(n-octylamine)],
[Zn(naphthenate)$_2$(n-octylamine)$_2$],
[Zn(naphthenate)$_2$(N,N-dibutylamine)],
[Zn(naphthenate)$_2$(N,N-dibutylamine)$_2$],
[Zn(naphthenate)$_2$(N,N-dimethyl-N-butylamine)$_2$],
[Zn(naphthenate)$_2$(N,N-dimethyl-N-butylamine)$_2$],
[Zn(naphthenate)$_2$(aminoethylaminopropyltrimethoxysilane)],
[Zn(naphthenate)$_2$(aminoethylaminopropyltrimethoxysilane)$_2$],
[Zn(naphthenate)$_2$(aminopropyltriethoxysilane)],
[Zn(naphthenate)$_2$(aminopropyltriethoxysilane)$_2$],
[Zn(neodecanoate)$_2$(di(n-octyl)amine)],
[Zn(neodecanoate)$_2$(di(n-octyl)amine)$_2$],
[Zn(neodecanoate)$_2$(n-octylamine)],
[Zn(neodecanoate)$_2$(n-octylamine)$_2$],
[Zn(neodecanoate)$_2$(N,N-dibutylamine)],
[Zn(neodecanoate)$_2$(N,N-dibutylamine)$_2$],
[Zn(neodecanoate)$_2$(3-aminopropyltrimethoxysilane)$_2$],
[Zn(neodecanoate)$_2$ (3-aminopropylmethyldiethoxysilane)$_2$],
[Zn(neodecanoate)$_2$ (aminoethylaminopropyltrimethoxysilane)],
[Zn(neodecanoate)$_2$ (aminoethylaminopropyltrimethoxysilane)$_2$],
[Zn(neodecanoate)$_2$ (aminopropyltriethoxysilane)],
[Zn(neodecanoate)$_2$ (aminopropyltriethoxysilane)$_2$],
[Zn(neodecanoate)$_2$ (bis(2-ethylhexyl)amine)],
[Zn(neodecanoate)$_2$ (bis(2-ethylhexyl)amine)$_2$],
[Zn(neodecanoate)$_2$ (diisononylamine)],
[Zn(neodecanoate)$_2$ (diisononylamine)$_2$],
[Zn(2-ethylhexanoate)$_2$(N,N-dibutylamine)],
[Zn(2-ethylhexanoate)$_2$(N,N-dibutylamine)$_2$],
[Zn(2-ethylhexanoate)$_2$(n-octylamine)],
[Zn(2-ethylhexanoate)$_2$(n-octylamine)$_2$],
[Zn(2-ethylhexanoate)$_2$ (bis(2-ethylhexyl)amine)],
[Zn(2-ethylhexanoate)$_2$ (bis(2-ethylhexyl)amine)$_2$],
[Zn(2-ethylhexanoate)$_2$ (diisononylamine)], or
[Zn(2-ethylhexanoate)$_2$ (diisononylamine)$_2$].

* * * * *